United States Patent
Mayoux et al.

(10) Patent No.: US 9,192,617 B2
(45) Date of Patent: Nov. 24, 2015

(54) PHARMACEUTICAL COMPOSITION, METHODS FOR TREATING AND USES THEREOF

(71) Applicants: Eric Williams Mayoux, Schemmerhofen (DE); Rolf Grempler, Birkenhard/Warthausen (DE); Thomas Klein, Radolfzell (DE)

(72) Inventors: Eric Williams Mayoux, Schemmerhofen (DE); Rolf Grempler, Birkenhard/Warthausen (DE); Thomas Klein, Radolfzell (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 38 days.

(21) Appl. No.: 13/833,097

(22) Filed: Mar. 15, 2013

(65) Prior Publication Data

US 2013/0252908 A1 Sep. 26, 2013

(30) Foreign Application Priority Data

Mar. 20, 2012 (EP) .................................... 12160377

(51) Int. Cl.
*A61K 31/7034* (2006.01)
*A61K 45/06* (2006.01)
*A61K 31/135* (2006.01)
*A61K 31/365* (2006.01)
*A61K 31/7048* (2006.01)
*A61K 9/20* (2006.01)

(52) U.S. Cl.
CPC ........... *A61K 31/7034* (2013.01); *A61K 31/135* (2013.01); *A61K 31/365* (2013.01); *A61K 31/7048* (2013.01); *A61K 45/06* (2013.01); *A61K 9/2018* (2013.01)

(58) Field of Classification Search
None
See application file for complete search history.

(56) References Cited

U.S. PATENT DOCUMENTS

| | | |
|---|---|---|
| 3,174,901 A | 3/1965 | Sterne |
| 3,884,906 A | 5/1975 | Van Der Meer et al. |
| 4,379,785 A | 4/1983 | Weyer et al. |
| 4,602,023 A | 7/1986 | Kiely et al. |
| 4,639,436 A | 1/1987 | Junge et al. |
| 4,786,023 A | 11/1988 | Harris et al. |
| 4,786,755 A | 11/1988 | Kiely et al. |
| 5,880,289 A | 3/1999 | Kaneko et al. |
| 6,414,126 B1 | 7/2002 | Ellsworth et al. |
| 6,498,193 B2 | 12/2002 | Beisswenger et al. |
| 6,515,117 B2 | 2/2003 | Ellsworth et al. |
| 6,613,806 B1 | 9/2003 | Aven et al. |
| 6,627,611 B2 | 9/2003 | Tomiyama et al. |
| 6,774,112 B2 | 8/2004 | Gougoutas |
| 6,794,480 B2 | 9/2004 | Goto et al. |
| 6,936,590 B2 | 8/2005 | Washburn et al. |
| 6,972,283 B2 | 12/2005 | Fujikura et al. |
| 7,101,856 B2 | 9/2006 | Glombik et al. |
| 7,169,761 B2 | 1/2007 | Tomiyama et al. |
| 7,202,350 B2 | 4/2007 | Imamura et al. |
| 7,371,732 B2 | 5/2008 | Eickelmann et al. |
| 7,375,087 B2 | 5/2008 | Teranishi et al. |
| 7,375,090 B2 | 5/2008 | Himmelsbach et al. |
| 7,375,213 B2 | 5/2008 | Deshpande et al. |
| 7,393,836 B2 | 7/2008 | Eckhardt et al. |
| 7,407,955 B2 | 8/2008 | Himmelsbach et al. |
| 7,417,032 B2 | 8/2008 | Eckhardt et al. |
| 7,419,959 B2 | 9/2008 | Eckhardt et al. |
| 7,541,341 B2 | 6/2009 | Fushimi et al. |
| 7,579,449 B2 | 8/2009 | Eckhardt et al. |
| 7,589,193 B2 | 9/2009 | Washburn et al. |
| 7,662,790 B2 | 2/2010 | Himmelsbach et al. |
| 7,674,486 B2 | 3/2010 | Bhaskaran et al. |
| 7,683,160 B2 | 3/2010 | Eckhardt et al. |
| 7,687,469 B2 | 3/2010 | Eckhardt et al. |
| 7,713,938 B2 | 5/2010 | Himmelsbach et al. |
| 7,723,309 B2 | 5/2010 | Himmelsbach et al. |
| 7,723,379 B2 | 5/2010 | Romanczyk, Jr. et al. |
| 7,745,414 B2 | 6/2010 | Eckhardt et al. |
| 7,772,191 B2 | 8/2010 | Eckhardt et al. |
| 7,772,192 B2 | 8/2010 | Esko |
| 7,772,378 B2 | 8/2010 | Himmelsbach et al. |
| 7,772,407 B2 | 8/2010 | Imamura et al. |
| 7,776,830 B2 | 8/2010 | Eckhardt et al. |
| 7,847,074 B2 | 12/2010 | Eckhardt et al. |
| 7,851,502 B2 | 12/2010 | Bindra et al. |
| 7,851,602 B2 | 12/2010 | Himmelsbach et al. |
| 7,858,587 B2 | 12/2010 | Eckhardt et al. |
| 7,879,806 B2 | 2/2011 | Himmelsbach et al. |
| 7,879,807 B2 | 2/2011 | Himmelsbach et al. |
| 8,039,441 B2 | 10/2011 | Himmelsbach et al. |
| 8,119,648 B2 | 2/2012 | Himmelsbach et al. |
| 8,178,541 B2 | 5/2012 | Himmelsbach et al. |
| 8,232,281 B2 | 7/2012 | Dugi et al. |
| 8,283,326 B2 | 10/2012 | Eckhardt et al. |

(Continued)

FOREIGN PATENT DOCUMENTS

| | | |
|---|---|---|
| CA | 2382480 A1 | 3/2001 |
| CA | 2388818 A1 | 4/2001 |

(Continued)

OTHER PUBLICATIONS

International Search Report for PCT/EP2012/052108 mailed Mar. 8, 2012.

(Continued)

*Primary Examiner* — Layla Bland
(74) *Attorney, Agent, or Firm* — Michael P. Morris; Edouard G. Lebel

(57) ABSTRACT

The invention relates to the treatment of metabolic disorders in an overweight or obese patient characterized in that empagliflozin and one or more antiobesity drugs are administered to the patient.

14 Claims, 5 Drawing Sheets

(56) References Cited

U.S. PATENT DOCUMENTS

| | | |
|---|---|---|
| 8,507,450 B2 | 8/2013 | Eckhardt et al. |
| 8,551,957 B2 | 10/2013 | Dugi et al. |
| 8,557,782 B2 | 10/2013 | Eckhardt et al. |
| 8,802,842 B2 | 8/2014 | Weber et al. |
| 2002/0137903 A1 | 9/2002 | Ellsworth et al. |
| 2003/0064935 A1 | 4/2003 | Gougoutas |
| 2003/0087843 A1 | 5/2003 | Washburn |
| 2003/0114390 A1 | 6/2003 | Washburn et al. |
| 2004/0138148 A1 | 7/2004 | Fushimi et al. |
| 2004/0138439 A1 | 7/2004 | Deshpande et al. |
| 2005/0065098 A1 | 3/2005 | Fujikura et al. |
| 2005/0085680 A1 | 4/2005 | Auerbach et al. |
| 2005/0124555 A1 | 6/2005 | Tomiyama et al. |
| 2005/0187168 A1 | 8/2005 | Eickelmann et al. |
| 2005/0209166 A1 | 9/2005 | Eckhardt et al. |
| 2005/0233982 A1 | 10/2005 | Himmelsbach et al. |
| 2006/0009400 A1 | 1/2006 | Eckhardt et al. |
| 2006/0019948 A1 | 1/2006 | Eckhardt et al. |
| 2006/0025349 A1 | 2/2006 | Eckhardt et al. |
| 2006/0035841 A1 | 2/2006 | Eckhardt et al. |
| 2006/0063722 A1 | 3/2006 | Washburn et al. |
| 2006/0074031 A1 | 4/2006 | Eckhardt et al. |
| 2006/0142210 A1 | 6/2006 | Eckhardt et al. |
| 2006/0189548 A1 | 8/2006 | Himmelsbach et al. |
| 2006/0210627 A1 | 9/2006 | Pfeffer et al. |
| 2006/0234953 A1 | 10/2006 | Himmelsbach et al. |
| 2006/0251728 A1 | 11/2006 | Himmelsbach et al. |
| 2006/0258749 A1 | 11/2006 | Eckhardt et al. |
| 2007/0004648 A1 | 1/2007 | Himmelsbach et al. |
| 2007/0027092 A1 | 2/2007 | Himmelsbach et al. |
| 2007/0049537 A1 | 3/2007 | Eckhardt et al. |
| 2007/0054867 A1 | 3/2007 | Eckhardt et al. |
| 2007/0073046 A1 | 3/2007 | Eckhardt et al. |
| 2007/0249544 A1 | 10/2007 | Himmelsbach et al. |
| 2007/0259821 A1 | 11/2007 | Eckhardt et al. |
| 2007/0281940 A1 | 12/2007 | Dugi et al. |
| 2008/0058379 A1 | 3/2008 | Eckhardt et al. |
| 2008/0107731 A1 | 5/2008 | Kohlrausch et al. |
| 2008/0234367 A1 | 9/2008 | Washburn et al. |
| 2008/0287529 A1 | 11/2008 | Deshpande et al. |
| 2009/0023913 A1 | 1/2009 | Eckhardt et al. |
| 2009/0137499 A1 | 5/2009 | Honda et al. |
| 2009/0281078 A1 | 11/2009 | Routledge et al. |
| 2009/0318547 A1 | 12/2009 | Eckhardt et al. |
| 2009/0326215 A1 | 12/2009 | Eckhardt et al. |
| 2010/0069310 A1 | 3/2010 | Himmelsbach et al. |
| 2010/0074950 A1 | 3/2010 | Sesha |
| 2010/0081625 A1 | 4/2010 | Wienrich et al. |
| 2010/0093654 A1 | 4/2010 | Himmelsbach et al. |
| 2010/0099641 A1 | 4/2010 | Himmelsbach et al. |
| 2010/0179191 A1 | 7/2010 | Himmelsbach et al. |
| 2010/0209506 A1 | 8/2010 | Eisenreich |
| 2010/0240879 A1 | 9/2010 | Eckhardt et al. |
| 2010/0249392 A1 | 9/2010 | Eckhardt et al. |
| 2010/0298243 A1 | 11/2010 | Manuchehri et al. |
| 2010/0317847 A1 | 12/2010 | Eckhardt et al. |
| 2011/0014284 A1 | 1/2011 | Eisenreich et al. |
| 2011/0046076 A1* | 2/2011 | Eickelmann et al. ........... 514/23 |
| 2011/0046087 A1 | 2/2011 | Eickelmann et al. |
| 2011/0065731 A1 | 3/2011 | Dugi et al. |
| 2011/0077212 A1 | 3/2011 | Seed et al. |
| 2011/0098240 A1 | 4/2011 | Dugi et al. |
| 2011/0178033 A1 | 7/2011 | Eckhardt et al. |
| 2011/0195917 A1 | 8/2011 | Dugi et al. |
| 2011/0206766 A1 | 8/2011 | Friedl et al. |
| 2011/0236477 A1 | 9/2011 | Schneider et al. |
| 2011/0237526 A1 | 9/2011 | Weber et al. |
| 2011/0237789 A1 | 9/2011 | Weber et al. |
| 2012/0041069 A1 | 2/2012 | Sesha |
| 2012/0071403 A1 | 3/2012 | Strumph et al. |
| 2012/0094894 A1 | 4/2012 | Graefe-Mody et al. |
| 2012/0196812 A1 | 8/2012 | Eickelmann et al. |
| 2012/0219622 A1 | 8/2012 | Kohlrausch et al. |
| 2012/0283169 A1 | 11/2012 | Grempler et al. |
| 2012/0296080 A1 | 11/2012 | Eckhardt et al. |
| 2013/0035281 A1 | 2/2013 | Klein et al. |
| 2013/0035298 A1 | 2/2013 | Broedl et al. |
| 2013/0035821 A1 | 2/2013 | Bonne et al. |
| 2013/0064887 A1 | 3/2013 | Ito et al. |
| 2013/0096076 A1 | 4/2013 | Dugi et al. |
| 2013/0137646 A1 | 5/2013 | Wienrich et al. |
| 2013/0236543 A1 | 9/2013 | Ito et al. |
| 2013/0252908 A1 | 9/2013 | Mayoux et al. |
| 2014/0031301 A1 | 1/2014 | Eickelmann et al. |
| 2014/0038911 A1 | 2/2014 | Eickelmann et al. |
| 2014/0046046 A1 | 2/2014 | Eckhardt et al. |
| 2014/0087996 A1 | 3/2014 | Klein et al. |
| 2014/0088027 A1 | 3/2014 | Grempler et al. |
| 2014/0256624 A1 | 9/2014 | Grempler et al. |
| 2014/0303097 A1 | 10/2014 | Broedl et al. |
| 2014/0303098 A1 | 10/2014 | Broedl et al. |
| 2014/0315832 A1 | 10/2014 | Broedl et al. |

FOREIGN PATENT DOCUMENTS

| | | |
|---|---|---|
| CA | 2402609 A1 | 9/2001 |
| CA | 2423568 A1 | 4/2002 |
| CA | 2437240 A1 | 8/2002 |
| CA | 2494177 A1 | 2/2004 |
| CA | 2496249 A1 | 3/2004 |
| CA | 2470365 A1 | 6/2004 |
| CA | 2508024 A1 | 6/2004 |
| CA | 2508226 A1 | 6/2004 |
| CA | 2526145 A1 | 9/2004 |
| CA | 2539032 A1 | 3/2005 |
| CA | 2548353 A1 | 7/2005 |
| CA | 2557269 A1 | 9/2005 |
| CA | 2557320 A1 | 9/2005 |
| CA | 2557801 A1 | 10/2005 |
| CA | 2569915 A1 | 1/2006 |
| CA | 2572149 A1 | 1/2006 |
| CA | 2572819 A1 | 1/2006 |
| CA | 2573777 A1 | 2/2006 |
| CA | 2574451 A1 | 2/2006 |
| CA | 2574500 A1 | 4/2006 |
| CA | 2649922 A1 | 11/2007 |
| CA | 2651019 A1 | 11/2007 |
| CA | 2720450 A1 | 10/2009 |
| DE | 2758025 A1 | 7/1979 |
| DE | 2951135 A1 | 6/1981 |
| EP | 0206567 A2 | 12/1986 |
| EP | 1224195 B | 7/2002 |
| EP | 1344780 A1 | 9/2003 |
| EP | 1385856 A | 2/2004 |
| EP | 1553094 A1 | 7/2005 |
| EP | 1564210 A1 | 8/2005 |
| EP | 1609785 A1 | 12/2005 |
| EP | 1791852 A2 | 6/2007 |
| EP | 1852108 A1 | 11/2007 |
| JP | 55007256 A | 1/1980 |
| JP | 56039056 A | 4/1981 |
| JP | 58164502 | 9/1983 |
| JP | 62030750 A | 2/1987 |
| JP | H1085502 A | 4/1998 |
| JP | 11124392 A | 5/1999 |
| JP | 2001288178 A | 10/2001 |
| JP | 2003511458 A | 3/2003 |
| JP | 2004196788 A | 7/2004 |
| JP | 2004359630 | 12/2004 |
| JP | 2005002092 A | 1/2005 |
| JP | 2005060625 A | 3/2005 |
| JP | 2008540373 A | 11/2008 |
| WO | 9831697 A1 | 7/1998 |
| WO | 0116147 A1 | 3/2001 |
| WO | 0127128 A1 | 4/2001 |
| WO | 0174834 A1 | 10/2001 |
| WO | 02064606 A1 | 8/2002 |
| WO | 02083066 A2 | 10/2002 |
| WO | 03020737 A1 | 3/2003 |
| WO | 03031458 A1 | 4/2003 |
| WO | 03078404 A1 | 9/2003 |
| WO | 03099836 A1 | 12/2003 |
| WO | 2004007517 A1 | 1/2004 |
| WO | 2004013118 A1 | 2/2004 |

(56) References Cited

FOREIGN PATENT DOCUMENTS

| | | |
|---|---|---|
| WO | 2004018468 A2 | 3/2004 |
| WO | 2004046115 A1 | 6/2004 |
| WO | 2004052902 A1 | 6/2004 |
| WO | 2004052903 A1 | 6/2004 |
| WO | 2004063209 A2 | 7/2004 |
| WO | 2004076470 A2 | 9/2004 |
| WO | 2004080990 A1 | 9/2004 |
| WO | 2005012318 A2 | 2/2005 |
| WO | 2005012326 A1 | 2/2005 |
| WO | 2005021566 A2 | 3/2005 |
| WO | 2005063785 A2 | 7/2005 |
| WO | 2005085237 A1 | 9/2005 |
| WO | 2005085265 A1 | 9/2005 |
| WO | 2005092877 A1 | 10/2005 |
| WO | 2006002912 A1 | 1/2006 |
| WO | 2006006496 A1 | 1/2006 |
| WO | 2006008038 A1 | 1/2006 |
| WO | 2006010557 A1 | 2/2006 |
| WO | 2006011469 A1 | 2/2006 |
| WO | 2006018150 A1 | 2/2006 |
| WO | 2006034489 A2 | 3/2006 |
| WO | 2006037537 A2 | 4/2006 |
| WO | 2006064033 A2 | 6/2006 |
| WO | 2006089872 A1 | 8/2006 |
| WO | 2006108842 A1 | 10/2006 |
| WO | 2006117359 A1 | 11/2006 |
| WO | 2006117360 A1 | 11/2006 |
| WO | 2006120208 A1 | 11/2006 |
| WO | 2007000445 A1 | 1/2007 |
| WO | 2007014894 A2 | 2/2007 |
| WO | 2007025943 A2 | 3/2007 |
| WO | 2007028814 A1 | 3/2007 |
| WO | 2007031548 A2 | 3/2007 |
| WO | 2007039417 A1 | 4/2007 |
| WO | 2007041053 A2 | 4/2007 |
| WO | 2007093610 A1 | 8/2007 |
| WO | 2007128724 A1 | 11/2007 |
| WO | 2007128749 A1 | 11/2007 |
| WO | 2007128761 A2 | 11/2007 |
| WO | 2007144175 A2 | 12/2007 |
| WO | 2008002905 A2 | 1/2008 |
| WO | 2008020011 A1 | 2/2008 |
| WO | 2008022267 A2 | 2/2008 |
| WO | 2008034859 A1 | 3/2008 |
| WO | 2008049923 A1 | 5/2008 |
| WO | 2008055870 A1 | 5/2008 |
| WO | 2008062273 A2 | 5/2008 |
| WO | WO 2008055940 A2 * | 5/2008 |
| WO | 2008089892 A1 | 7/2008 |
| WO | 2008090210 A1 | 7/2008 |
| WO | 2008101938 A1 | 8/2008 |
| WO | 2008101939 A1 | 8/2008 |
| WO | 2008101943 A1 | 8/2008 |
| WO | 2008116179 A1 | 9/2008 |
| WO | 2008116195 A2 | 9/2008 |
| WO | 2008131149 A2 | 10/2008 |
| WO | 2009022007 A1 | 2/2009 |
| WO | 2009022010 A1 | 2/2009 |
| WO | 2009035969 A1 | 3/2009 |
| WO | 2009091082 A1 | 7/2009 |
| WO | 2009099734 A1 | 8/2009 |
| WO | 2009121945 A2 | 10/2009 |
| WO | 2010045656 A2 | 4/2010 |
| WO | 2010092123 A1 | 8/2010 |
| WO | 2010092124 A1 | 8/2010 |
| WO | 2010092125 A1 | 8/2010 |
| WO | 2010092126 A1 | 8/2010 |
| WO | 2010119990 A1 | 10/2010 |
| WO | 2010138535 A1 | 12/2010 |
| WO | 2011039107 A1 | 4/2011 |
| WO | 2011039108 A2 | 4/2011 |
| WO | 2011039337 A1 | 4/2011 |
| WO | 2011060290 A2 | 5/2011 |
| WO | 2011120923 A1 | 10/2011 |
| WO | 2012031124 A2 | 3/2012 |
| WO | 2012062698 A1 | 5/2012 |
| WO | 2012106303 A1 | 8/2012 |
| WO | 2012107476 A1 | 8/2012 |
| WO | 2012120040 A1 | 9/2012 |
| WO | 2013007557 A1 | 1/2013 |
| WO | 2013131967 A1 | 9/2013 |
| WO | 2013139777 A1 | 9/2013 |

OTHER PUBLICATIONS

International Search Report for PCT/EP2012/053910 mailed May 14, 2012.

International Search Report for PCT/EP2012/060194 mailed on Jul. 17, 2012.

International Search Report for PCT/EP2012/062922 mailed Aug. 14, 2012.

International Search Report for PCT/EP2013/054524 mailed on May 6, 2013.

International Search Report for PCT/EP2013/055671 mailed Apr. 16, 2013.

Isaji, Masayuki "Sodium-glucose cotransporter inhibitors for diabetes" Current Opinion in Investigational Drugs, (2007) vol. 8, No. 4, pp. 285-292.

Jabbour, Serge A. "The Importance of Reducing Hyperglycemia While Preserving Insulin Secretion—The Rational for Sodium-coupled Glucose Co-trnasporter 2 Inhibition in Diabetes" Touch Briefings, US Endocrinology (2009) pp. 75-78.

Jagdmann Jr, G. Erik ; Synthesis of 5-(4-Substituted Benzyl)-2,4-Diaminoquinazolines as Inhibitors of *Candida albicans* Dihydrofolate Reductase; Journal Heterocyclic Chemical (1995) vol. 32 pp. 1461-1465.

Jones, Byrony "Empagliflozin—one step closer to glycaemic control in patients with type II diabetes and CKD?" (2014) Nature Reviews Nephrology 10, 181, 2 pgs.

Joshi, Shashank R. "Metformin: Old Wine in New Bottle—Evolving Technology and Therapy in Diabetes" Journal of Association of Physicians in India, (2005) vol. 53, pp. 963-972.

Kadowaki, T et al. "PPAR gamma agonist and antagonist" Nihon Yakurigaku Zasshi (2001) vol. 118, No. 9, pp. 321-326. (English abstract).

Knochel, Paul et al. "Highly functionalized Organomagnesium Reagents Prepared through Halogen-Metal Exchange" Angew. Chem. INt. Ed. (2003) vol. 42, 4302-4320.

Koo, Ja Seo., et al; 2-Pyridyl Cyanate: A Useful Reagent for he Preparation of Nitriles; Synthetic Communications (1996) vol. 26 No. 20 pp. 3709-3713; Marcel Dekker, Inc.

Krasovskiy Arkady et al. "A LiCL-Mediated Br/Mg Exchange Reaction for the Preparation of Functionalized Aryl- and Heterarylmagnesium Compounds from Organic Bromides" Angew. Chem. Int. Ed. (2004) vol. 43, pp. 3333-3336.

Kuribayashi, Takeshi., et al; Bis C-Glycosylated Diphenylmethanes for Stable Glycoepitope Mimetics; Syntletters (1999) vol. 6 pp. 737-740.

Kuribayashi, Takeshi., et al; c-Glycosylated Aryl tins: Versatile Building Blocks for Aryl C-Glycoside Glycomimetics; J. Carbohydrate Chemistry (1999) vol. 18, No. 4 pp. 371-382.

Kuribayashi, Takeshi., et al; C-Glycosylated Diphenylmethanes and Benzophenones: The Stille Coupling Reaction of C-Glycosylated Aryl tins with Benzyl Bromides and Acid Chlorides; J. Carbohydrate Chemistry (1999) vol. 18, No. 4 pp. 393-401.

Langle, Sandrine., et al; Selective Double Suzuki Cross-Coupling Reactions. Synthesis of Unsymmetrical Diaryl (or Heteroaryl) Methanes; Tetrahedron Letters (2003) vol. 44 pp. 9255-9258; Pergamon Press.

Lehmann, Ule et al. "Palladium-Catalyzed Cross-Coupling Reactions between Dihydropyranylindium Reagents and Aryl Halides, Synthesis of C-Aryl Glycals" Organic Letters, 2003, vol. 5, No. 14, pp. 2405-2408.

Li, T, et al. "Lack of Pharmacokinetic Interaction between Dapagliflozin and Pioglitazone in Healthy Subjects" Journal of Clinical Pharmacology, (2009) vol. 49, No. 9, pp. 1093.

(56) References Cited

OTHER PUBLICATIONS

Lieberman, Joseph A. "Metabolic Changes Associated with Antipsychotic Use" Prim Care Companion J Clinc Psychiatry (2004) 6, pp. 8-13.
Lipworth, Brian J. "Clinical pharmacology of b3-adrenoceptors" Br J Clin Pharmacol (1996) pp. 291-300.
Maayan, Lawrence et al. "Effectiveness of Medications Used to Attenuate Antipsychotic-Related Weight Gain and Metabolic Antipsychotic-Related Weight Gain and Metabolic Abnormalities: A Systematic Review and Meta-Analysis" (2010) Neuropsychopharmacology, vol. 35, pp. 1520-1530.
Magee, G.M. et al. "Is hyperfiltration associated with the future risk of developing diabetic nephropathy? A meta-analysis" Diabetologia (2009) 52: pp. 691-697.
Malatiali, Slava et al. "Phlorizin Prevents Glomerular Hyperfiltration but not Hypertrophy in Diabetic Rats" (2008) Experimental Diabetes Research, vol. 2008, 7 pgs.
McHale, Mary "Grignard Reaction" Connexions module: m15245, (2007) pp. 1-18.
McLaughlin, Mark., et al; Suzuki-Miyaura Cross-Coupling of Benzylic Phosphahates with Arylboronic Acids; Organic Letters (2005) vol. 7 No. 22 pp. 4875-4878.
McMaster University, Chem2006 Lab Manual, 1997/98, Expt 1, Part B, pp. 1-9.
Meng, Wei et al "Discovery of Dapagliflozin: A Potent, Selective Renal Sodium-Dependent Glucose Cotransporter 2 (SGLT2) Inhibitor for the Treatment of Type 2 Diabetes" J. Med. Chem. (2008) vol. 51, pp. 1145-1149.
Merck Manual Online Edition, "Diabetes Mellitus" http://www.merckmanuals.com/professional/endocrine_and_metabolic_disorders/diabetes_mellitus_and_disorders of carbohyrate_metabolism/diabetes_mellitus_dm.html#v987998. last revision Jun. 2008 by Preeti Kishore M.D.
Merriam-Webster's Collegiate Dictionary,definition of prevent, published 1998 by Merriam-Webster Inc. p. 924.
Miller, Del D. "Review and Management of Clozapine Side Effects" (2000) J Clinc Psychiatry, 61 (Suppl 8) pp. 14-17.
Mooradian, Arsharg D. et al. "Narrative Review: A Rational Approach to Starting Insulin Therapy" (2006) Annals of Internal Medicine, vol. 145, pp. 125-134.
Neamati, Ouri., et al;, "Depsides and Depsidones as Inhibiton of HIV-1 Integrase: Dimvery of Novel Inhibitors Through 3D Database Searclung", J. Med. Chem., 1997, vol. 40, pp. 942-951.
Nobre, Sabrina M., et al; Synthesis of Diarylmethane Derivatives from Pd-Catalyzed Cross-Coupling Reactions of Benzylic Halides with Arylboronic Acids; Tetrahedron Letters (2004) vol. 45 8225-8228.
Oku, Akira., et al; T-1095, An Inhibitor or renal Na+-Glucose Cotransporters, May Provide a Novel Approach to Treating Diabetes; Diabetes (1999) vol. 48 pp. 1794-1800.
Panchapakesan, Usha et al. Effects of SGLT2 Inhibition in Human Kidney Proximal Tubular Cells—Renoprotection in Diabetic Nephropathy? PLOS one, (2013) vol. 8, Issue 2, e54442, 8 pgs.
Patil, Basanagouda M. et al. "Elevation of systolic blood pressure in an animal model of olanzapine induced weight gain" (2006) European Journal of Pharmacology, vol. 551, pp. 112-115.
Perner, Richard J., et al; 5,6,7-Trisubstituted 4-Aminopyrido[2,3-d]pyrimidines as Novel inhibitors of Adenosime Kinase; Journal of Medicinal Chemistry (2003) vol. 46 pp. 5249-5257.
Piya, Milan K. et al. "Emerging treatment options for type 2 diabetes" British Journal of Clinical Pharmacology, (2010) vol. 70, No. 5, pp. 631-644.
Powers, Richard E. et al. "Understanding the Side Effects of Neuroleptics" (2008) Bureau of Geriatric Psychiatry/ DETA, pp. 17-24.
Printz, Richard L. et al. "Tweaking the Glucose Sensor: Adjusting Glucokinase Activity with Activator Compounds" Endocrinology, (2005) vol. 146, No. 9, pp. 3693-3695.
Rainier, Jon D. et al. "Aluminum- and Boron-Mediated C-Glycoside Synthesis from 1,2-Anhydroglycosides" Organic Letters, (2000) vol. 2, No. 17, pp. 2707-2709.
Randzio, Stanislaw L. et al. "Metastability and Instability of Organic Crystalline Substances" J. Phys. Chem. (2008) 112, pp. 1435-1444.
Redenti, Enrico et al. "Drug/Cyclodextrin/Hydroxy Acid Multicomponent Systems. Properties and Pharmaceutical Applications" Journal of Pharmaceutical Sciences, (2000) vol. 89, No. 1, pp. 1-8.
Revesz, Lasslo., et al; SAR of Benzoylpylpyridines and Benzophenones as p38 Alpha MAP Kinase Inhibitors with Oral Activity; Bioorganic & Medicinal Chemistry Letters (2004) vol. 14 pp. 3601-3605.
Rieusset, Jennifer et al. "Insulin Acutely Regulates the Expression of the Peroxisome Proliferator-Activated Receptor-y in Human Adipocytes" (1999) Diabetes, vol. 48, pp. 699-705.
Ritchie, C.W. et al. "The impact upon extra-pyramidal side effects, clinical symptoms and quality of life of a switch from conventional to atypical antipsychotics (risperidone or olanzapine) in elderly patients with schizophrenia" (2003) International Journal of Geriatric Psychiatry, vol. 18, pp. 432-440.
Rudnic, Edward et al. "Oral Solid Dosage Forms" Remington's Pharmaceutical Sciences, 18th Ed, Gennaro, A.R. Ed, Macie Pub. Co. (1990) pp. 1633-1665.
Abstract ASN09L1_307a "Contact View (TH-P0751) Kidney Function and Response to Diabetes in Mice Lacking SGLT2", Vallon, Volker et al, Oct. 29, 2009, 1 pg.
Abstract ASN09L1_4153a, "Contact View (SA-P02723) Chronic SGLT2 Blockade Reduces Proximal Reabsorption and Normalizes State of Tubuloglomerular Feedback Activation in Hyperfiltering Diabetic Rats" Thomson, Scott et al., Oct. 31, 2009, 1 pg.
Adachi, Tetsuya., et al; T-1095, A Renal Na+-Glucose Transporter Inhibitor, Improves Hyperglycemia in Streptozotocin-Induced Diabetic Rats; Metabolism (2000) vol. 49 No. 8 pp. 990-995.
American Diabetes Association "Consensus Development Conference on Antipyschotic Drugs and Obesity and Diabetes" (2004) Diabetes Care, vol. 27, No. 2, pp. 596-601.
American Diabetes Association "Diagnosis and Classification of Diabetes Mellitus" Diabetes Care, vol. 33, Supplement 1, Jan. 2010. pp. S62-S69.
Anonymous "Efficacy and Safety of Empagliflozin (BI 10773) in Patients with Type 2 Diabetes and Renal Impairment" Jan. 8, 2013, XP055120166, www.clinicaltrials.gov/ct2/show/study/NCT01164501?term=empagliflozin&rank=26.
Anonymous "Prevalence of Chronic Kidney Disease and Associated Risk Factors—United States, 1999-2004", Mar. 2, 2007, XP055119515, http://www.cdc.gov/mmwr/preview/mmwrhtml/mm5608a2.htm.
Ault Addison, "Techniques and experiments for organic chemistry" University Science Books, 1998, pp. 59-60.
Banker, Gilbert S. et al. "Modern Pharmaceutics, Third Edition, Revised and Expanded" (1996) Marcel Dekker, p. 596.
Baptista, Trino et al. "Pharmacological Management of Atypical Antipsychotic-Induced Weight Gain" (2008) CNS Drugs, 22, 6, pp. 478-495.
Barnett, Anthony H. et al. "Efficacy and safety of empagliflozin added to existing antidiabetes treatments in patients with type 2 diabetes and chronic kidney disease: a randomised, double-blind, placebo-controlled trial" The Lancet, (2014) vol. 2, pp. 369-384.
Benhaddou, Rachida., et al; Tetra-n-Propylammonium Tetra-Oxoruthenate(VII): A Reagent of Choice for the Oxidation of Diversely Protected Glycopyranoses and Glycofuranoses to Lactones; Carbohydrate Research (1994) vol. 260 pp. 243-250.
Bloomgarden, Zachary T. "Diabetes Treatment" Diabetes Care, (Mar. 2009) vol. 32, No. 3 pp. e25-e30.
Boyda, Heidi N et al. "Preclinical models of antipsychotic drug-induced metabolic side effects" (2010) Trends in Pharmacological Sciences vol. 31, pp. 484-497.
Buhler, Volker "Kollidon® Polyvinylpyrrolidone excipients for the pharmaceutical industry" 9th revised edition, Mar. 2008, 1-331.
Byrn, Stephen et al. "Pharmaceutical Solids: A Strategic Approach to Regulatory Considerations" Pharmaceutical Research, vol. 12, No. 7, (1995) pp. 945-954.

(56) References Cited

OTHER PUBLICATIONS

Castelhano, Arlindo L. et al. "Reactions of an Electrophilic Glycine Cation Equivalent With Grignard Reagents a Simple Synthesis of β,g-Unsaturated Amino Acids" (1986) Tetrahedron Letters, vol. 27, No. 22, pp. 2435-2438.

Cernea Simona. et al. "β-Cell Protection and Therapy for Latent Autoimmune Diabetes in Adults" Diabetes Care (2009) vol. 32, Supplement 2, pp. S246-S252.

Deacon, Carolyn F. "Perspectives in Diabetes Therapeutic Strategies Based on Glucagon-Like Peptide 1" Diabetes, (2004) vol. 53 pp. 2181-2189.

Diabetes Mellitus, Merck Manual Online Edition, (retrieved Sep. 13, 2011) http://www.merckmanuals.com/professional/endocrine_and_metabolic_disorders/diabetes_mellitus_and_disorders_of_carbohydrate_metabolism/diabetes_mellitus_dm.html#v987998. Revision Jun. 2008.

Dohle, Wolfgang., et al; Copper-Mediated Cross-Coupling of Functionalized Arylmagnesium Reagents with Functionalized Alkyl and Benzylic Halides; Organic Letters (2001) vol. 3 No. 18 pp. 2871-2873.

Drug Watch "Type 2 Diabetes Mellitus" Formulary vol. 43 Aug. 2008 p. 304.

Ellinger, Lara K. et al. "Efficacy of Metformin and Topiramate in Prevention and Treatment of Second-Generation Antipsychotic-Induced Weight Gain" Annals of Pharmacotherapy (2010) vol. 44, No. 4, pp. 668-679.

EMBASE Database. Accession No. 0050872772. Jelsing, J et al. "Empagliflozin a novel sodium glucose cotransporter-2 inhibitor improves glucose homeostasis and preserves pancreatic beta cell mass in db/db mice" (2012) 2 pgs.

EMBASE database: Accession No. 0050781595. Jelsing, Jacob et al. "The sodium glucose cotransporter-2 (SGLT-2) inhibitor empagliflozin has a durable effect on the restoration of glucose homeostasis by preserving beta-cell mass in zucker diabetic fatty rats" (2012) 2 pgs.

Ettmayer, Peter et al. "Lessons Learned from Marketed and Investigational Prodrugs" (2004) Journal of Medicinal Chemistry, vol. 47, No. 10, pp. 2393-2404.

Fuerstner, Alois., et al; Practical Method for the Rhodium-Catalyzed Addition of Aryl- and Alkenylboronic Acids to Aldehydes; Advanced Synthesis and Catalysis (2001) vol. 343 No. 4 pp. 343-350.

Fujimori, Yoshikazu et al. "Remogliflozin Etabonate in a Novel Category of Selective Low-Affinity Sodium Glucose Cotransporter (SGLT2) Inhibitors, Exhibits Antidiabetic Efficacy in Rodent Models" (2008) Journal of Pharmacology and Experimental Therapeutics vol. 327 No. 1, pp. 268-276.

Ghassemi et al. "Synthesis and properties of new sulfonated poly(p-phenylene) derivatives for proton exchange membranes" Polymer (2004) pp. 5847-5854.

Goodwin, Nicole C. et al. "Novel L-Xylose Derivatives as Selective Sodium-Dependent Glucose Cotransporter 2 (SGLT2) Inhibitors for the Treatment of Type 2 Diabetes" (2009) Journal Medicinal Chemistry vol. 52 pp. 6201-6204.

Graefe-Mody, E.U., et al., "Evaluation of the potential for steady-state pharmacokinectic and pharmacodynamic interactions between the DPP-4 inhibitor linagliptin and metformin in healthy subjects". Current Medical Research and Opinion, Informa Healthcare, GB, vol. 25. No. 8, Aug. 1, 2009, pp. 1963-1972.

Greco, Gary T. et al. "Segregation of Active Constituents from Tablet Formulations During Grinding: Theoretical Considerations" Drug Development and Industrial Pharmacy, (1982) 8(4), pp. 565-578.

Hasnain, Mehrul et al. "Metformin for Atypical Antipsychotic-Induced Weight Gain and Glucose Metabolism Dysregulation—Review of Literature and Clinical Suggestions" (2010) CNS Drugs, 24(3), pp. 194-206.

Hatsuda, Asanori., et al; A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.

Henderson, David C. et al. "Clozapine and Hypertension: A Chart Review of 82 Patients" (2004) J Clin Psychiatry, 65, pp. 686-689.

Hussey, Elizabeth K. et al. "Safety, Pharmacokinetics and Pharmacodynamics of Remogliflozin Etabonate (SGLT2 Inhibitor) and Metformin When Co-Administered in Type 2 Diabetes Mellitus (T2DM) Patients" Diabetes, American Diabetes Association, (2009) XP00913667, vol. 58, p. A157.

Hutton, Craig A., et al; A Convenient Preparation of dityrosine Via Miyaura Borylation-Suzuki Coupling of Iodotyrosine Derivatives; Tetrahedron Letters (2003) vol. 44 pp. 4895-4898; Pergamon Press.

Iida, Takehiko., et al; Tributylmagnesium Ate Complex-Mediated Novel Bromine—Magnesium Exchange Reaction for Selective Monosubstitution of Dibromoarenes; Tetrahedron Letters (2001) vol. 42 pp. 4841-4844; Pergamon Press.

International Search Report for PCT/EP2005/002618 mailed Jun. 30, 2005.

International Search Report for PCT/EP2006/061956 mailed on Jul. 5, 2006.

International Search report for PCT/EP2006/061957 mailed on Jul. 5, 2006.

International Search Report for PCT/EP2006/062191 mailed Aug. 8, 2006.

International Search Report for PCT/EP2007/062023 mailed Sep. 17, 2008.

International Search Report for PCT/EP2010/051734 mailed Jun. 8, 2010.

International Search Report for PCT/EP2010/051735 mailed May 20, 2010.

International Search Report for PCT/EP2010/051736 mailed May 7, 2010.

International Search Report for PCT/EP2010/051737 mailed May 7, 2010.

International Search Report for PCT/EP2010/064619 mailed Jan. 20, 2011.

International Search Report for PCT/EP2011/054734 mailed Aug. 12, 2011.

International Search Report for PCT/EP2011/069532 mailed Dec. 15, 2011.

Sherwin, Robert S. et al. "The Prevention or Delay of Type 2 Diabetes" Diabetes Care, (2002) vol. 25, No. 4, pp. 742-749.

Silverman, et al. "Handbook of Grignard Reagents" Marcel Dekker (1996) p. 82.

Singhal, Dharmendra et al. "Drug polymorphism and dosage form design: a practical perspective" Advanced Drug Delivery Reviews, 56, (2004) pp. 335-347.

Sommer, Michael Bech., et al; displacement of Halogen of 2-Halogeno-Substituted Benzonitriles with Carbonions. Preparation of (2-Cyanoaryl)arylacetonitriles; Journal of Organic Chemistry (1990) vol. 55 pp. 4817-4821.

Stazi, Federica., et al; Statistical Experimental Design-Driven Discovery of room-Temperature Conditions for Palladium-Catalyzed Cyanation of Aryl Bromides; Tetrahedron Letters (2005) vol. 46 1815-1818; Elsevier Ltd.

Stella, Valentino J. "Prodrugs as therapeutics" (2004) Ashley Publications, vol. 14, No. 3, pp. 277-280.

Svegliati-Baroni, Gianluca et al. "Glucagon-like peptide-1 receptor activation stimulates hepatic lipid oxidation and restores hepatic signalling alteration induced by a high-fat diet in nonalcholic steatohepatitis" (2011) LIver International, vol. 31, 9, pp. 1285-1297.

Tanaka, Chikako "Therapeutic Drugs for Metabolic Diseases, Chapter 2" (2002) New Yakurigaku (New Pharmacology) pp. 524-527.

Testa, Bernard "Prodrug research: futile or fertile?" (2004) Biochemical Pharmacology vol. 68, pp. 2097-2106.

Thomas, Leo et al. "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics (2008) 325, pp. 175-182.

(56) References Cited

OTHER PUBLICATIONS

Thomson, Scott C. et al. "Acute and chronic effects of SGLT2 blockade on glomerular and tubular function in the early diabetic rat" (2011) Am J Physiol Regul Integr Comp Physiol, V 302, pp. R75-R83.

Threlfall, Terry "Structural and Thermodynamic Explanations of Ostwald's Rule" Organic Process Research & Development (2003) vol. 7, pp. 1017-1027.

Tsujihara, Kenji et al. "Na+-Glucose Cotransporter (SGLT) Inhibitors as Antidiabetic Agents. 4. Synthesis and Pharmacological Properties of 4'-Dehydroxyphlorizin Derivatives Substituted on the B Ring" J. Med. Chem. (1999) vol. 42, pp. 5311-5324.

Tykwinski, Rik R; Evolution in the Palladium-Catalyzed Cross-Coupling of sp- and sp2-Hybridized Carbon Atoms; Angew Chemical International Edition (2003) vol. 42 pp. 1566-1568.

Ueta, Kiichiro., et al; Long-Term Treatment with the Na+-Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.

Unknown "Intensification of Development of SGLT inhibitor—New Alternative of Antidiabetic" Aug. 21, 2007; 2 pgs; http://www.yakuji.co.jp/entry4100.html.

Vallon, Volker et al. "Glomerular Hyperfiltration in Experimental Diabetes Melliutes: Potential Role of Tubular Reabsorption" (1999) J. Am. Soc. Nephrol., V 10: pp. 2569-2576.

Vallon, Volker et al. "SGLT2 inhibitor empagliflozin reduces renal growth and albuminuria in proportion to hyperglycemia and prevents glomerular hyperfiltration in diabetic Akita mice" (2013) Am J Physiol Renal Physiol, 306, F194-F204.

Vervoort, G. et al. "Glomerular hyperfiltration in type 1 diabetes mellitus results from primary changes in proximal tubular sodium handling without changes in volume expansion" (2005) European Journal of Clinical Investigation vol. 35, pp. 330-336.

Wallace, Debra J., et al; Cyclopropylboronic Acid: Synthesis and Suzuki Cross-Coupling Reactions; Tetrahedron Letters (2002) vol. 43 pp. 6987-6990; Pergamon Press.

Wang Y et al: "BI-1356. Dipeptidyl-peptidase IV inhibitor, antidiabetic agent" Drugs of the Future, Prous Science, ES,vol. 33, No. 6, Jun. 1, 2008, pp. 473-477.

Websters Third New International Dictionary, Editor: Gove, definition of prevent; 1963, 2 pgs.

Wolff, Manfred E., et al., "Burger's Medicinal Chemistry and Drug Discovery, Fifth Edition, vol. 1, Principles and Practices", (1995) Wiley-Interscience Publication pp. 975-977.

Woo, Young Sup et al. "Blood pressure changes during clozapine or olanzapine treatment in Korean schizophrenic patients" (2009) The World Journal of Biological Psychiatry, vol. 10(4); pp. 420-425.

Wu, Ren-Rong et al. "Lifestyle Intervention and Metformin for Treatment of Antipsychotic-Induced Weight Gain, A Randomized Controlled Trial" Journal of American Medical Association (2008) V 299, pp. 185-193.

Xue, Song., et al; Zinc-mediated Synthesis of Alpha-C-Glycosided from 1,2-Anhydroglycosides; Synletters (2003) vol. 6 pp. 870-872.

Yamada, Yuichiro et al. "Clinic: Careful Progress in the Field and new Therapeutic Methods" Medical Online, (2007) vol. 220, No. 13, pp. 1219-1221.

Yao, Chun-Hsu et al. "Discovery of Novel N-b-D-Xylosylindole Derivatives as Sodium-Dependent Glucose Cotransporter 2 (SGLT2) Inhibitors for the Management of Hyperglycemia in Diabetes" (2011) J. Med. Chem. vol. 54, pp. 166-178.

Zhang, L. et al "Dapagliflozin treatment in patients with different stages of type 2 diabetes mellitus: effects on glycaemic control and body weight" Diabetes, Obesity and Metabolism (2010) vol. 12, No. 6, p. 510-515.

\* cited by examiner

Significant differences from the vehicle-treated group are denoted by: p<0.01, *p<0.001.
Significant differences from the empagliflozin group are denoted by † p<0.05, †† p<0.01, †††
p<0.001. Significant difference from the orlistat group are denoted by $ p<0.05, $$ p <0.01.

Figure 2a

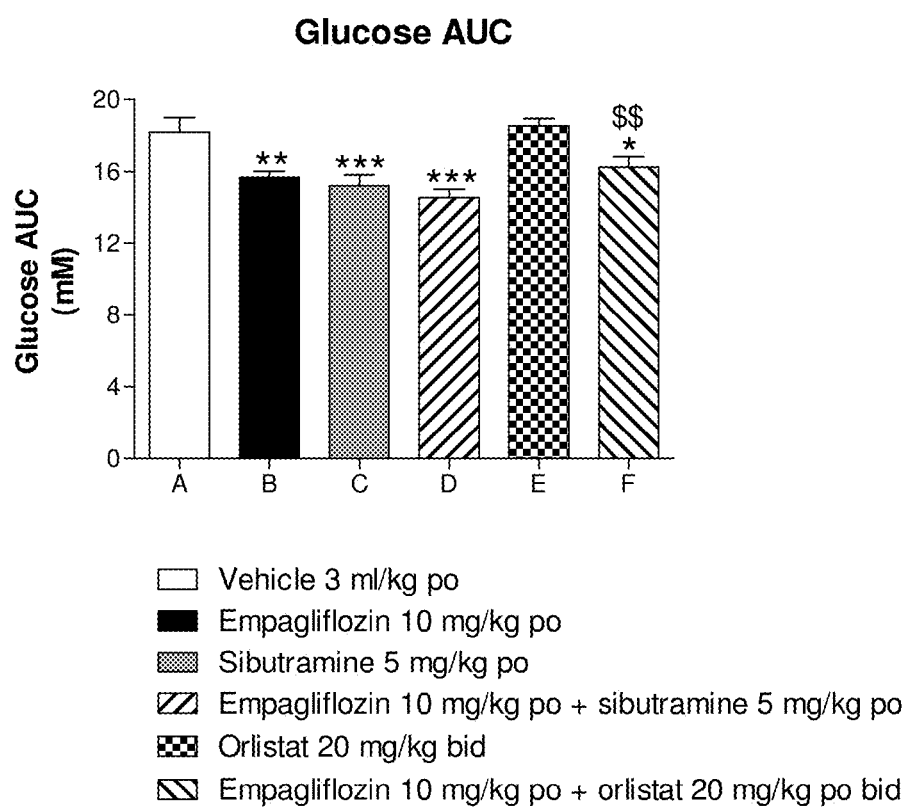

☐ Vehicle 3 ml/kg po
■ Empagliflozin 10 mg/kg po
▦ Sibutramine 5 mg/kg po
▨ Empagliflozin 10 mg/kg po + sibutramine 5 mg/kg po
▩ Orlistat 20 mg/kg bid
▧ Empagliflozin 10 mg/kg po + orlistat 20 mg/kg po bid Significant differences from the vehicle-treated group are denoted by: $p<0.01$, *$p<0.001$.
Significant differences from the empagliflozin group are denoted by † $p<0.05$, †† $p<0.01$, ††† $p<0.001$. Significant differences from the orlistat group are denoted by $ $p<0.05$, $$ $p<0.01$.

Significant differences from the vehicle-treated group are denoted by: p<0.01, *p<0.001.
Significant differences from the empagliflozin group are denoted by † p<0.05, †† p<0.01, †††
p<0.001. Significant differences from the orlistat group are denoted by $ p<0.05, $$ p <0.01.

Figure 3a

|  | Glucose (mM) | Insulin (ng/ml) |
|---|---|---|
|  | Mean ± SEM | Mean ± SEM |
| Vehicle | 7.09 ± 0.30 | 2.04 ± 0.33 |
| Empagliflozin (10 mg/kg po) | 6.75 ± 0.15 | 1.34 ± 0.15 * |
| Sibutramine (5 mg/kg po) | 6.08 ± 0.17 *** | 0.95 ± 0.12 *** |
| Empagliflozin / sibutramine | 5.73 ± 0.31 ***††† | 0.82 ± 0.12 ***† |
| Orlistat (20 mgk/g po bid) | 6.77 ± 0.19 | 1.47 ± 0.19 |
| Empagliflozin / orlistat | 6.27 ± 0.17 ** | 0.94 ± 0.15 ***$ |

|  | Leptin (ng/ml) | True TAG (nM) |
|---|---|---|
|  | Mean ± SEM | Mean ± SEM |
| Vehicle | 14.1 ± 1.5 | 0.263 ± 0.05 |
| Empagliflozin (10 mg/kg po) | 12.2 ± 1.3 | 0.193 ± 0.03 |
| Sibutramine (5 mg/kg po) | 10.2 ± 1.3 * | 0.186 ± 0.03 |
| Empagliflozin / sibutramine | 7.8 ± 1.1 ***† | 0.166 ± 0.04 * |
| Orlistat (20 mgk/g po bid) | 10.3 ± 0.8 * | 0.323 ± 0.04 |
| Empagliflozin / orlistat | 6.3 ± 0.9 ***††$ | 0.271 ± 0.04 |

Samples were taken after an overnight fast. Significant differences from the vehicle-treated group are denoted by: *$p<0.05$, $p<0.01$, *$p<0.001$. Significant differences from the empagliflozin group are denoted by † $p<0.05$, †† $p<0.01$. Significant differences from the pioglitazone group are denoted by $ $p<0.05$, $$ $p<0.01$.

Figure 3b

|  | Water (g) | Fat (g) | Protein (g) |
|---|---|---|---|
|  | Mean ± SEM | Mean ± SEM | Mean ± SEM |
| Vehicle | 211.0 ± 2.1 | 116.4 ± 7.1 | 68.2 ± 0.9 |
| Empagliflozin (10 mg/kg po) | 209.0 ± 3.8 | 113.8 ± 2.7 | 66.4 ± 1.0 |
| Sibutramine (5 mg/kg po) | 204.8 ± 3.4 | 95.5 ± 4.6 * | 67.1 ± 1.2 |
| Empagliflozin / sibutramine | 207.6 ± 2.8 | 75.2 ± 6.0 ***†††$ | 68.1 ± 0.9 |
| Orlistat (20 mgk/g po bid) | 216.3 ± 3.5 | 93.7 ± 4.4 * | 69.9 ± 1.4 |
| Empagliflozin / orlistat | 206.9 ± 2.1 | 88.4 ± 7.8 **†† | 66.9 ± 0.8 |

Significant differences from the vehicle-treated group are denoted by: *$p<0.05$, $p<0.01$, *$p<0.001$. Significant differences from the empagliflozin group are denoted by †† $p<0.01$, ††† $p<0.001$. Significant differences from the sibutramine group are denoted by $ $p<0.05$.

PHARMACEUTICAL COMPOSITION, METHODS FOR TREATING AND USES THEREOF

TECHNICAL FIELD OF THE INVENTION

The invention relates to a pharmaceutical composition comprising empagliflozin and one or more antiobesity drugs as described hereinafter which is suitable in the treatment or prevention of one or more conditions selected from diabetes mellitus, impaired glucose tolerance, impaired fasting blood glucose, hyperglycemia, obesity, overweight, inter alia.

Furthermore the invention relates to methods
- for preventing, slowing progression of, delaying, or treating a metabolic disorder;
- for improving glycemic control and/or for reducing of fasting plasma glucose, of postprandial plasma glucose and/or of glycosylated hemoglobin HbA1c;
- for preventing, slowing, delaying or reversing progression from impaired glucose tolerance, impaired fasting blood glucose, insulin resistance and/or from metabolic syndrome to type 2 diabetes mellitus;
- for preventing, slowing progression of, delaying or treating of a condition or disorder selected from the group consisting of complications of diabetes mellitus;
- for reducing body weight and/or body fat, or preventing an increase in body weight and/or body fat, or facilitating a reduction in body weight and/or body fat;
- for preventing or treating the degeneration of pancreatic beta cells and/or for improving and/or restoring the functionality of pancreatic beta cells and/or restoring the functionality of pancreatic insulin secretion;
- for preventing, slowing, delaying or treating diseases or conditions attributed to an abnormal accumulation of ectopic fat;
- maintaining and/or improving the insulin sensitivity and/or for treating or preventing hyperinsulinemia and/or insulin resistance;
- for preventing, slowing progression of, delaying, or treating new onset diabetes after transplantation (NODAT) and/or post-transplant metabolic syndrome (PTMS);
- for preventing, delaying, or reducing NODAT and/or PTMS associated complications including micro- and macrovascular diseases and events, graft rejection, infection, and death;
- for treating hyperuricemia and hyperuricemia associated conditions;
- for treating or preventing kidney stones;
- for treating hyponatremia;

in patients in need thereof characterized in that a pharmaceutical composition comprising an SGLT2 inhibitor and one or more antiobesity drugs as defined hereinafter is administered.

In addition the present invention relates to the use of empagliflozin and one or more antiobesity drugs for the manufacture of a medicament for use in a method as described hereinbefore and hereinafter.

The invention also relates to a use of a pharmaceutical composition according to this invention for the manufacture of a medicament for use in a method as described hereinbefore and hereinafter.

BACKGROUND OF THE INVENTION

The rising prevalences of obesity and type 2 diabetes mellitus (T2DM) represent major challenges for global public health. Worldwide, there are more than 400 million adults with a body mass index (BMI) exceeding 30 kg/m² (defining "obesity") and 220 million with type 2 diabetes mellitus, figures which are projected to rise to 700 million and 366 million, respectively, by 2030 (World Health Organisation 2010; International Diabetes Federation 2010). According to the US Centers for Disease Control and Prevention, rates of type 2 diabetes mellitus have tripled in the past 30 years. This is caused largely by the global epidemic of obesity, a major risk factor for developing type 2 diabetes mellitus and prediabetes. Diabetes now affects an estimated 23.6 million people in the United States; another 57 million have prediabetes. Prediabetes raises short-term absolute risk of type 2 diabetes mellitus five- to sixfold. The development of type 2 diabetes mellitus can be delayed or sometimes prevented in individuals with obesity who are able to lose weight. In patients with type 2 diabetes mellitus, weight loss improves glycemic control and cardiovascular disease risk factors.

Type 2 diabetes mellitus is an increasingly prevalent disease that due to a high frequency of complications leads to a significant reduction of life expectancy. Because of diabetes-associated microvascular complications, type 2 diabetes is currently the most frequent cause of adult-onset loss of vision, renal failure, and amputations in the industrialized world. In addition, the presence of type 2 diabetes mellitus is associated with a two to five fold increase in cardiovascular disease risk.

After long duration of disease, most patients with type 2 diabetes mellitus will eventually fail on oral therapy and become insulin dependent with the necessity for daily injections and multiple daily glucose measurements.

The UKPDS (United Kingdom Prospective Diabetes Study) demonstrated that intensive treatment with metformin, sulfonylureas or insulin resulted in only a limited improvement of glycemic control (difference in HbA1c~0.9%). In addition, even in patients within the intensive treatment arm glycemic control deteriorated significantly over time and this was attributed to deterioration of β-cell function. Importantly, intensive treatment was not associated with a significant reduction in macrovascular complications, i.e. cardiovascular events. Therefore many patients with type 2 diabetes mellitus remain inadequately treated, partly because of limitations in long term efficacy, tolerability and dosing inconvenience of existing antihyperglycemic therapies.

Oral antidiabetic drugs conventionally used in therapy (such as e.g. first- or second-line, and/or mono- or (initial or add-on) combination therapy) include, without being restricted thereto, metformin, sulphonylureas, thiazolidinediones, glinides and α-glucosidase inhibitors.

The high incidence of therapeutic failure is a major contributor to the high rate of long-term hyperglycemia-associated complications or chronic damages (including micro- and macrovascular complications such as e.g. diabetic nephropathy, retinopathy or neuropathy, or cardiovascular complications) in patients with type 2 diabetes mellitus.

Therefore, there is an unmet medical need for methods, medicaments and pharmaceutical compositions with a good efficacy with regard to glycemic control, with regard to disease-modifying properties and with regard to reduction of cardiovascular morbidity and mortality while at the same time showing an improved safety profile.

Empagliflozin is a novel SGLT2 inhibitor that is described for the treatment or improvement in glycemic control in patients with type 2 diabetes mellitus, for example in WO 05/092877, WO 06/117359, WO 06/120208, WO 2010/092126, WO 2010/092123, WO 2011/039107, WO 2011/039108. The use of a SGLT2 inhibitor in a method for treating obesity is described in WO 08/116,195 for example.

AIM OF THE PRESENT INVENTION

An aim of the present invention is to provide a pharmaceutical composition, dosage form or method for slowing the progression of, delaying or treating of pre-diabetes in a patient diagnosed of being overweight or obese.

Another aim of the present invention is to provide a pharmaceutical composition, dosage form or method for treating a metabolic disorder in a patient diagnosed of being overweight or obese.

Another aim of the present invention is to provide a pharmaceutical composition, dosage form or method for improving glycemic control or for reducing of fasting plasma glucose, of postprandial plasma glucose or of glycosylated hemoglobin HbA1c in a patient diagnosed of being overweight or obese.

Another aim of the present invention is to provide a pharmaceutical composition, dosage form or method for reducing body weight or body fat, or preventing an increase in body weight and/or body fat, or facilitating a reduction in body weight or body fat, in a patient diagnosed of being overweight or obese.

Another aim of the present invention is to provide a pharmaceutical composition, dosage form or method for treating of overweight or obesity in a patient diagnosed of having one or more conditions selected from the group consisting of pre-diabetes, type 2 diabetes mellitus (T2DM), impaired glucose tolerance (IGT), impaired fasting blood glucose (IFG), hyperglycemia, postprandial hyperglycemia, hyperinsulinemia and metabolic syndrome.

Further aims of the present invention become apparent to the one skilled in the art by description hereinbefore and in the following and by the examples.

SUMMARY OF THE INVENTION

Within the scope of the present invention it has now been found that a combination of empagliflozin and one or more antiobesity drugs as defined herein, including the respective pharmaceutical compositions, uses and methods of treatment according to this invention, have particularly advantageous properties, which make them suitable for the purpose of this invention and/or for fulfilling one or more of above needs. In particular it has been found that a combination of empagliflozin and one or more antiobesity drugs leads to an increased body weight reduction compared with a treatment of the antiobesity drug alone. In particular a reduction of the body fat is observed which is more pronounced than in the respective mono-therapies with empagliflozin or the antiobesity drug alone. No significant changes in body water or body protein content are observed. At the same time hyperglycemia is reduced and glycemic control and insulin sensitivity improved. Therefore a combination of a empagliflozin and one or more antiobesity drugs as defined herein is particularly suitable in the treatment of hyperglycemia, diabetes mellitus and of hyperglycemia and diabetes mellitus related conditions and complications in patients being diagnosed of being overweight or obese. Furthermore due to an improvement of the glycemic parameters, such as the glucose tolerance, the plasma insulin levels and the fasting blood glucose, the combination of empagliflozin and one or more antiobesity drugs as defined herein is particularly suitable in the treatment of pre-diabetes and the prevention of type 2 diabetes mellitus and type 2 diabetes mellitus related conditions and complications and the like in patients being overweight or obese. This opens up new therapeutic possibilities in the treatment of overweight and obesity as well as in the prevention of type 2 diabetes mellitus, complications of diabetes mellitus and of neighboring disease states.

Therefore, in a first aspect the present invention provides a method for preventing, slowing the progression of, delaying or treating a metabolic disorder selected from the group consisting of type 2 diabetes mellitus, impaired glucose tolerance, impaired fasting blood glucose, hyperglycemia, postprandial hyperglycemia, hyperinsulinemia and metabolic syndrome in a patient diagnosed of being overweight or obese characterized in that empagliflozin and one or more antiobesity drugs are administered to the patient.

According to another aspect the present invention provides a method for slowing the progression of, delaying or treating of pre-diabetes in a patient diagnosed of being overweight or obese characterized in that empagliflozin and one or more antiobesity drugs are administered to the patient.

According to another aspect the present invention provides a method for preventing, slowing the progression of, delaying or treating of an onset of type 2 diabetes mellitus in a patient diagnosed of being overweight or obese in need thereof characterized in that empagliflozin and one or more antiobesity drugs are administered to the patient.

According to another aspect the present invention provides a method for treating of overweight or obesity in a patient diagnosed of having one or more conditions selected from the group consisting of pre-diabetes, type 2 diabetes mellitus, impaired glucose tolerance, impaired fasting blood glucose, hyperglycemia, postprandial hyperglycemia, hyperinsulinemia and metabolic syndrome characterized in that empagliflozin and one or more antiobesity drugs are administered to the patient.

According to another aspect of the invention, there is provided a method for improving glycemic control and/or for reducing of fasting plasma glucose, of postprandial plasma glucose and/or of glycosylated hemoglobin HbA1c in a patient diagnosed of being overweight or obese characterized in that empagliflozin and one or more antiobesity drugs are administered to the patient.

The combination according to this invention may also have valuable disease-modifying properties with respect to diseases or conditions related to impaired glucose tolerance, impaired fasting blood glucose, insulin resistance and/or metabolic syndrome, in particular in patients being diagnosed of being overweight or obese.

According to another aspect of the invention, there is provided a method for preventing, slowing, delaying or reversing progression from impaired glucose tolerance, impaired fasting blood glucose, insulin resistance or from metabolic syndrome to type 2 diabetes mellitus in a patient diagnosed of being overweight or obese characterized in that empagliflozin and one or more antiobesity drugs are administered to the patient.

As by the use of a combination according to this invention, an improvement of the glycemic control in patients diagnosed of being overweight or obese is obtainable, also those conditions and diseases related to or caused by an increased blood glucose level may be treated in those patients.

According to another aspect of the invention, there is provided a method for preventing, slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, diabetic foot, dyslipidemia, arteriosclerosis, myocardial infarction, accute coronary syndrome, unstable angina pectoris, stable angina pectoris, stroke, peripheral arterial occlusive disease, cardiomyopathy, heart failure, heart rhythm disorders and vascular restenosis, in a patient diagnosed of being overweight or obese characterized in that empagliflozin and one or more antiobesity drugs are administered to the patient. In particular one or more aspects of diabetic nephropathy such as hyperperfusion, proteinuria and albuminuria may be treated, their progression slowed or their onset delayed or prevented. The term "tissue ischaemia" particularly comprises diabetic macroangiopathy, diabetic microangiopathy, impaired wound healing and diabetic ulcer. The terms "micro- and macrovascular diseases" and "micro- and macrovascular complications" are used interchangeably in this application.

By the use of a combination according to this invention and due to the activity of empagliflozin as an SGLT2 inhibitor excessive blood glucose levels are not converted to insoluble storage forms, like fat, but excreted through the urine of the patient. In animal models it can be seen that loss of body fat accounts for the majority of the observed weight loss whereas no significant changes in body water or protein content are observed. Therefore, no gain in weight or even a reduction in body weight is the result.

According to another aspect of the invention, there is provided a method for reducing body weight and/or body fat, or preventing an increase in body weight and/or body fat, or facilitating a reduction in body weight and/or body fat, in a patient diagnosed of being overweight or obese characterized in that empagliflozin and one or more antiobesity drugs are administered to the patient.

The pharmacological effect of empagliflozin as an SGLT2 inhibitor in the combination according to this invention is independent of insulin. Therefore, an improvement of the glycemic control is possible without an additional strain on the pancreatic beta cells. By an administration of a pharmaceutical composition according to this invention a beta-cell degeneration and a decline of beta-cell functionality such as for example apoptosis or necrosis of pancreatic beta cells can be delayed or prevented. Furthermore, the functionality of pancreatic cells can be improved or restored, and the number and size of pancreatic beta cells increased. It may be shown that the differentiation status and hyperplasia of pancreatic beta-cells disturbed by hyperglycemia can be normalized by treatment with a pharmaceutical composition according to this invention.

According to another aspect of the invention, there is provided a method for preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion in a patient diagnosed of being overweight or obese characterized in that empagliflozin and one or more antiobesity drugs are administered to the patient.

By the use of a combination according to the present invention, an abnormal accumulation of ectopic fat, in particular of the liver, may be reduced or inhibited. Therefore, according to another aspect of the present invention, there is provided a method for preventing, slowing, delaying or treating diseases or conditions attributed to an abnormal accumulation of ectopic fat, in particular liver fat, in a patient diagnosed of being overweight or obese characterized in that empagliflozin and one or more antiobesity drugs are administered to the patient. Diseases or conditions which are attributed to an abnormal accumulation of liver fat are particularly selected from the group consisting of general fatty liver, non-alcoholic fatty liver (NAFL), non-alcoholic steatohepatitis (NASH), hyperalimentation-induced fatty liver, diabetic fatty liver, alcoholic-induced fatty liver and toxic fatty liver.

As a result thereof, another aspect of the invention provides a method for maintaining and/or improving the insulin sensitivity and/or for treating or preventing hyperinsulinemia and/or insulin resistance in a patient diagnosed of being overweight or obese characterized in that empagliflozin and one or more antiobesity drugs are administered to the patient.

According to another preferred embodiment of the present invention, there is provided a method for improving glycemic control in patients, in particular in adult patients, who are diagnosed of being overweight or obese and in addition diagnosed of having pre-diabetes or type 2 diabetes mellitus, as an adjunct to and exercise.

According to another aspect of the invention there is provided the use of empagliflozin and one or more antiobesity drugs for the manufacture of a medicament for preventing, slowing the progression of, delaying or treating a metabolic disorder selected from the group consisting of type 2 diabetes mellitus, impaired glucose tolerance, impaired fasting blood glucose, hyperglycemia, postprandial hyperglycemia, hyperinsulinemia and metabolic syndrome; or slowing the progression of, delaying or treating of pre-diabetes; or preventing, slowing the progression of, delaying or treating of an onset of type 2 diabetes mellitus; or improving glycemic control and/or for reducing of fasting plasma glucose, of postprandial plasma glucose and/or of glycosylated hemoglobin HbA1c; or preventing, slowing, delaying or reversing progression from impaired glucose tolerance, impaired fasting blood glucose, insulin resistance or from metabolic syndrome to type 2 diabetes mellitus; or preventing, slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, diabetic foot, dyslipidemia, arteriosclerosis, myocardial infarction, accute coronary syndrome, unstable angina pectoris, stable angina pectoris, stroke, peripheral arterial occlusive disease, cardiomyopathy, heart failure, heart rhythm disorders and vascular restenosis; or reducing body weight and/or body fat, or preventing an increase in body weight and/or body fat, or facilitating a reduction in body weight and/or body fat; or preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion; or preventing, slowing, delaying or treating diseases or conditions attributed to an abnormal accumulation of ectopic fat, in particular liver fat; or for maintaining and/or improving the insulin sensitivity and/or for treating or preventing hyperinsulinemia and/or insulin resistance;

in a patient being diagnosed of being overweight or obese and in need thereof characterized in that empagliflozin and the one or more antiobesity drugs are administered, as defined hereinbefore and hereinafter.

According to another aspect of the invention there is provided the use of empagliflozin and one or more antiobesity drugs for the manufacture of a medicament for treating of overweight or obesity in a patient diagnosed of having one or more conditions selected from the group consisting of pre-diabetes, type 2 diabetes mellitus, impaired glucose tolerance, impaired fasting blood glucose, hyperglycemia, postprandial hyperglycemia, hyperinsulinemia and metabolic syndrome characterized in that empagliflozin and one or more antiobesity drugs are administered to the patient.

According to another aspect of the invention, there is provided a pharmaceutical composition comprising empagliflozin and one or more antiobesity drugs and one or more pharmaceutically acceptable excipients.

According to another aspect of the invention, there is provided a pharmaceutical dosage form comprising empagliflozin and one or more antiobesity drugs and one or more pharmaceutically acceptable excipients.

According to another aspect of the invention, there is provided the use of a pharmaceutical composition according to the present invention for the manufacture of a medicament for a therapeutic or preventive method as described hereinbefore and hereinafter.

According to another aspect of the invention, there is provided a pharmaceutical composition according to the present invention for the use in a treatment and/or prevention and/or therapeutic and/or preventive method as described hereinbefore and hereinafter.

DEFINITIONS

The term "active ingredient" of a pharmaceutical composition according to the present invention means the SGLT2 inhibitor according to the present invention. An "active ingredient is also sometimes referred to herein as an "active substance".

The term "body mass index" or "BMI" of a human patient is defined as the weight in kilograms divided by the square of the height in meters, such that BMI has units of $kg/m^2$.

The term "overweight" is defined as the condition wherein the individual has a BMI greater than or 25 $kg/m^2$ and less than 30 $kg/m^2$. The terms "overweight" and "pre-obese" are used interchangeably.

The terms "obesity" or "being obese" and the like are defined as the condition wherein the individual has a BMI equal to or greater than 30 $kg/m^2$. According to a WHO definition the term obesity may be categorized as follows: the term "class I obesity" is the condition wherein the BMI is equal to or greater than 30 $kg/m^2$ but lower than 35 $kg/m^2$; the term "class II obesity" is the condition wherein the BMI is equal to or greater than 35 $kg/m^2$ but lower than 40 $kg/m^2$; the term "class III obesity" is the condition wherein the BMI is equal to or greater than 40 $kg/m^2$.

The indication obesity includes in particular exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity, central obesity, visceral obesity, abdominal obesity.

The term "visceral obesity" is defined as the condition wherein a waist-to-hip ratio of greater than or equal to 1.0 in men and 0.8 in women is measured. It defines the risk for insulin resistance and the development of pre-diabetes.

The term "abdominal obesity" is usually defined as the condition wherein the waist circumference is >40 inches or 102 cm in men, and is >35 inches or 94 cm in women. With regard to a Japanese ethnicity or Japanese patients abdominal obesity may be defined as waist circumference 85 cm in men and 90 cm in women (see e.g. investigating committee for the diagnosis of metabolic syndrome in Japan).

The term "euglycemia" is defined as the condition in which a subject has a fasting blood glucose concentration within the normal range, greater than 70 mg/dL (3.89 mmol/L) and less than 100 mg/dL (5.6 mmol/L). The word "fasting" has the usual meaning as a medical term.

The term "hyperglycemia" is defined as the condition in which a subject has a fasting blood glucose concentration above the normal range, greater than 100 mg/dL (5.6 mmol/L). The word "fasting" has the usual meaning as a medical term.

The term "hypoglycemia" is defined as the condition in which a subject has a blood glucose concentration below the normal range, in particular below 70 mg/dL (3.89 mmol/L).

The term "postprandial hyperglycemia" is defined as the condition in which a subject has a 2 hour postprandial blood glucose or serum glucose concentration greater than 200 mg/dL (11.11 mmol/L).

The term "impaired fasting blood glucose" or "IFG" is defined as the condition in which a subject has a fasting blood glucose concentration or fasting serum glucose concentration in a range from 100 to 125 mg/dl (i.e. from 5.6 to 6.9 mmol/l), in particular greater than 110 mg/dL and less than 126 mg/dl (7.00 mmol/L). A subject with "normal fasting glucose" has a fasting glucose concentration smaller than 100 mg/dl, i.e. smaller than 5.6 mmol/l.

The term "impaired glucose tolerance" or "IGT" is defined as the condition in which a subject has a 2 hour postprandial blood glucose or serum glucose concentration greater than 140 mg/dl (7.78 mmol/L) and less than 200 mg/dL (11.11 mmol/L). The abnormal glucose tolerance, i.e. the 2 hour postprandial blood glucose or serum glucose concentration can be measured as the blood sugar level in mg of glucose per dL of plasma 2 hours after taking 75 g of glucose after a fast. A subject with "normal glucose tolerance" has a 2 hour postprandial blood glucose or serum glucose concentration smaller than 140 mg/dl (7.78 mmol/L).

The term "hyperinsulinemia" is defined as the condition in which a subject with insulin resistance, with or without euglycemia, has fasting or postprandial serum or plasma insulin concentration elevated above that of normal, lean individuals without insulin resistance, having a waist-to-hip ratio <1.0 (for men) or <0.8 (for women).

The terms "insulin-sensitizing", "insulin resistance-improving" or "insulin resistance-lowering" are synonymous and used interchangeably.

The term "insulin resistance" is defined as a state in which circulating insulin levels in excess of the normal response to a glucose load are required to maintain the euglycemic state (Ford E S, et al. *JAMA*. (2002) 287:356-9). A method of determining insulin resistance is the euglycaemic-hyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. With this method, it is not possible to distinguish between hepatic and peripheral insulin resistance.

Furthermore, insulin resistance, the response of a patient with insulin resistance to therapy, insulin sensitivity and hyperinsulinemia may be quantified by assessing the "homeostasis model assessment to insulin resistance (HOMA-IR)" score, a reliable indicator of insulin resistance (Katsuki A, et al. Diabetes Care 2001; 24: 362-5). Further reference is made to methods for the determination of the HOMA-index for insulin sensitivity (Matthews et al., *Diabetologia* 1985, 28:412-19), of the ratio of intact proinsulin to insulin (Forst et al., *Diabetes* 2003, 52(Suppl. 1): A459) and to an euglycemic clamp study. In addition, plasma adiponectin levels can be monitored as a potential surrogate of insulin sensitivity. The estimate of insulin resistance by the homeostasis assessment model (HOMA)-IR score is calculated with the formula (Galvin P, et al. Diabet Med 1992; 9:921-8):

HOMA-IR=[fasting serum insulin(µU/mL)]×[fasting plasma glucose(mmol/L)/22.5]

Insulin resistance can be confirmed in these individuals by calculating the HOMA-IR score. For the purpose of this invention, insulin resistance is defined as the clinical condition in which an individual has a HOMA-IR score >4.0 or a HOMA-IR score above the upper limit of normal as defined for the laboratory performing the glucose and insulin assays.

As a rule, other parameters are used in everyday clinical practice to assess insulin resistance. Preferably, the patient's triglyceride concentration is used, for example, as increased triglyceride levels correlate significantly with the presence of insulin resistance.

Individuals likely to have insulin resistance are those who have two or more of the following attributes: 1) overweight or obese, 2) high blood pressure, 3) hyperlipidemia, 4) one or more $1^{st}$ degree relative with a diagnosis of IGT or IFG or type 2 diabetes.

Patients with a predisposition for the development of IGT or IFG or type 2 diabetes are those having euglycemia with hyperinsulinemia and are by definition, insulin resistant. A typical patient with insulin resistance is usually overweight or obese. If insulin resistance can be detected, this is a particularly strong indication of the presence of pre-diabetes. Thus, it may be that in order to maintain glucose homoeostasis a person needs 2-3 times as much insulin as a healthy person, without this resulting in any clinical symptoms.

"Pre-diabetes" is a general term that refers to an intermediate stage between normal glucose tolerance (NGT) and overt type 2 diabetes mellitus (T2DM), also referred to as intermediate hyperglycaemia. As such, it represents 3 groups of individuals, those with impaired glucose tolerance (IGT) alone, those with impaired fasting glucose (IFG) alone or those with both IGT and IFG. IGT and IFG usually have distinct pathophysiologic etiologies, however also a mixed condition with features of both can exist in patients. Therefore in the context of the present invention a patient being diagnosed of having "pre-diabetes" is an individual with diagnosed IGT or diagnosed IFG or diagnosed with both IGT and IFG. Following the definition according to the American Diabetes Association (ADA) and in the context of the present invention a patient being diagnosed of having "pre-diabetes" is an individual with:

a) a fasting plasma glucose (FPG) concentration <100 mg/dL [1 mg/dL=0.05555 mmol/L] and a 2-hour plasma glucose (PG) concentration, measured by a 75-g oral glucose tolerance test (OGTT), ranging between ≥140 mg/dL and <200 mg/dL (i.e., IGT); or
b) a fasting plasma glucose (FPG) concentration between ≥100 mg/dL and <126 mg/dL and a 2-hour plasma glucose (PG) concentration, measured by a 75-g oral glucose tolerance test (OGTT) of <140 mg/dL (i.e., IFG); or
c) a fasting plasma glucose (FPG) concentration between ≥100 mg/dL and <126 mg/dL and a 2-hour plasma glucose (PG) concentration, measured by a 75-g oral glucose tolerance test (OGTT), ranging between ≥140 mg/dL and <200 mg/dL (i.e., both IGT and IFG).

Patients with "pre-diabetes" are individuals being pre-disposed to the development of type 2 diabetes. Pre-diabetes extends the definition of IGT to include individuals with a fasting blood glucose within the high normal range ≥100 mg/dL (J. B. Meigs, et al. Diabetes 2003; 52:1475-1484). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749).

The methods to investigate the function of pancreatic beta-cells are similar to the above methods with regard to insulin sensitivity, hyperinsulinemia or insulin resistance: An improvement of beta-cell function can be measured for example by determining a HOMA-index for beta-cell function (Matthews et al., *Diabetologia* 1985, 28:412-19), the ratio of intact proinsulin to insulin (Forst et al., *Diabetes* 2003, 52(Suppl. 1): A459), the insulin/C-peptide secretion after an oral glucose tolerance test or a meal tolerance test, or by employing a hyperglycemic clamp study and/or minimal modeling after a frequently sampled intravenous glucose tolerance test (Stumvoll et al., *Eur J Clin Invest* 2001, 31: 380-81).

The term "type 2 diabetes mellitus" or "T2DM" is defined as the condition in which a subject has a fasting blood glucose or serum glucose concentration greater than 125 mg/dL (6.94 mmol/L). The measurement of blood glucose values is a standard procedure in routine medical analysis. If a glucose tolerance test is carried out, the blood sugar level of a diabetic will be in excess of 200 mg of glucose per dL (11.1 mmol/l) of plasma 2 hours after 75 g of glucose have been taken on an empty stomach. In a glucose tolerance test 75 g of glucose are administered orally to the patient being tested after 10-12 hours of fasting and the blood sugar level is recorded immediately before taking the glucose and 1 and 2 hours after taking it. In a healthy subject, the blood sugar level before taking the glucose will be between 60 and 110 mg per dL of plasma, less than 200 mg per dL 1 hour after taking the glucose and less than 140 mg per dL after 2 hours. If after 2 hours the value is between 140 and 200 mg, this is regarded as abnormal glucose tolerance.

The term "late stage type 2 diabetes mellitus" includes patients with a secondary drug failure, indication for insulin therapy and progression to micro- and macrovascular complications e.g. diabetic nephropathy, or coronary heart disease (CHD).

The term "HbA1c" refers to the product of a non-enzymatic glycation of the haemoglobin B chain. Its determination is well known to one skilled in the art. In monitoring the treatment of diabetes mellitus the HbA1c value is of exceptional importance. As its production depends essentially on the blood sugar level and the life of the erythrocytes, the HbA1c in the sense of a "blood sugar memory" reflects the average blood sugar levels of the preceding 4-6 weeks. Diabetic patients whose HbA1c value is consistently well adjusted by intensive diabetes treatment (i.e. <6.5% of the total haemoglobin in the sample), are significantly better protected against diabetic microangiopathy. For example, metformin on its own achieves an average improvement in the HbA1c value in the diabetic of the order of 1.0-1.5%. This reduction of the HbA1C value is not sufficient in all diabetics to achieve the desired target range of <6.5% and preferably <6% HbA1c.

The term "insufficient glycemic control" or "inadequate glycemic control" in the scope of the present invention means a condition wherein patients show HbA1c values above 6.5%, in particular above 7.0%, even more preferably above 7.5%, especially above 8%.

The "metabolic syndrome", also called "syndrome X" (when used in the context of a metabolic disorder), also called the "dysmetabolic syndrome" is a syndrome complex with the cardinal feature being insulin resistance (Laaksonen D E, et al. *Am J Epidemiol* 2002; 156:1070-7). According to the ATP III/NCEP guidelines (Executive Summary of the Third Report of the National Cholesterol Education Program (NCEP) Expert Panel on Detection, Evaluation, and Treatment of High Blood Cholesterol in Adults (Adult Treatment Panel III) *JAMA: Journal of the American Medical Association* (2001) 285:2486-2497), diagnosis of the metabolic syndrome is made when three or more of the following risk factors are present:

1. Abdominal obesity, defined as waist circumference >40 inches or 102 cm in men, and >35 inches or 94 cm in women; or with regard to a Japanese ethnicity or Japanese patients defined as waist circumference ≥85 cm in men and ≥90 cm in women;
2. Triglycerides: ≥150 mg/dL
3. HDL-cholesterol <40 mg/dL in men
4. Blood pressure ≥130/85 mm Hg (SBP≥130 or DBP≥85)
5. Fasting blood glucose ≥100 mg/dL The NCEP definitions have been validated (Laaksonen D E, et al. *Am J. Epidemiol.* (2002) 156:1070-7). Triglycerides and HDL cholesterol in the blood can also be determined by standard methods in medical analysis and are described for example in Thomas L (Editor): "Labor and Diagnose", TH-Books Verlagsgesellschaft mbH, Frankfurt/Main, 2000.

According to a commonly used definition, hypertension is diagnosed if the systolic blood pressure (SBP) exceeds a value of 140 mm Hg and diastolic blood pressure (DBP) exceeds a value of 90 mm Hg. If a patient is suffering from manifest diabetes it is currently recommended that the systolic blood pressure be reduced to a level below 130 mm Hg and the diastolic blood pressure be lowered to below 80 mm Hg.

The term "empagliflozin" refers to the SGLT2 inhibitor 1-chloro-4-(β-D-glucopyranos-1-yl)-2-[4-((S)-tetrahydrofuran-3-yloxy)-benzyl]-benzene of the formula

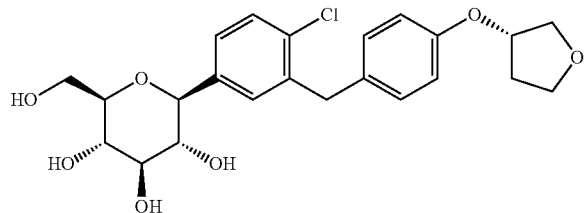 [SMILES: OC[C@H]1O[C@@H](c2ccc(Cl)c(Cc3ccc(O[C@H]4CCOC4)cc3)c2)[C@H](O)[C@@H](O)[C@@H]1O]

as described for example in WO 2005/092877. Methods of synthesis are described in the literature, for example WO 06/120208 and WO 2011/039108. According to this invention, it is to be understood that the definition of empagliflozin also comprises its hydrates, solvates and polymorphic forms thereof, and prodrugs thereof. An advantageous crystalline form of empagliflozin is described in WO 2006/117359 and WO 2011/039107 which hereby are incorporated herein in their entirety. This crystalline form possesses good solubility properties which enables a good bioavailability of the SGLT2 inhibitor. Furthermore, the crystalline form is physico-chemically stable and thus provides a good shelf-life stability of the pharmaceutical composition. Preferred pharmaceutical compositions, such as solid formulations for oral administration, for example tablets, are described in WO 2010/092126, which hereby is incorporated herein in its entirety.

The term "antiobesity drug" as used herein is defined as a therapeutic agent, including a mixture of one or more such therapeutic agents, for the treatment of overweight or obesity. Treatment of overweight or obesity by therapeutic agents, including mixtures thereof, can be achieved for example by decreasing appetite or food intake, increasing metabolic rate or affecting metabolism or acting on the gastrointestinal tract. Examples of various classes of antiobesity drugs are antagonists of the cannabinoid receptor, GPR119 agonists, MCH-1 receptor antagonists, MC4 receptor agonists, NPY5 or NPY2 antagonists, β3-receptor agonists, lipase inhibitors, lipid metabolizing enzyme modulators (e.g., diacylglycerol acyltransferase, fatty acid synthase inhibitor, acetyl-CoA carboxylase inhibitors, stearoyl-CoA desaturase inhibitors, etc.), leptin or leptin mimetics, agonists of the 5HT2c receptor, glucagon-like peptide-1 (GLP-1) receptor agonists, cholecystokinin-A (CCK-A) agonists, ghrelin antagonists. Examples of drugs for obesity include sibutramine, orlistat (a lipase inhibitor), cetilistat (a lipase inhibitor), a combination of phentermine (a psychostimulant appetite suppressor) and topiramate (an anticonvulsant which also increases the sensation of feeling full), a combination of naltrexone (an opioid receptor antagonist) and bupropion (an atypical antidepressant and smoking cessation aid), lorcaserin (a selective 5-HT$_{2C}$ receptor agonist supposed to activate proopiomelanocortin [POMC] production and consequently promote weight loss through satiety) as well as liraglutide (a GLP-1 analogue).

The antiobesity drug may be present in the form of a pharmaceutically acceptable salt. The antiobesity drug or a pharmaceutically acceptable salt thereof may be present in the form of a solvate such as a hydrate or alcohol adduct. Combinations of two or more drugs may be in the form a free combination or a fixed dose combination for example. With respect to the antiobesity drug the methods of synthesis are known to the skilled person and are described in the scientific literature and/or in published patent documents.

The terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy.

The terms "prophylactically treating", "preventivally treating" and "preventing" are used interchangeably and comprise a treatment of patients at risk to develop a condition mentioned hereinbefore, thus reducing said risk.

The term "tablet" comprises tablets without a coating and tablets with one or more coatings. Furthermore the "term" tablet comprises tablets having one, two, three or even more layers and press-coated tablets, wherein each of the beforementioned types of tablets may be without or with one or more coatings. The term "tablet" also comprises mini, melt, chewable, effervescent and orally disintegrating tablets.

The terms "pharmacopoe" and "pharmacopoeias" refer to standard pharmacopoeias such as the "USP 31-NF 26 through Second Supplement" (United States Pharmacopeial Convention) or the "European Pharmacopoeia 6.3" (European Directorate for the Quality of Medicines and Health Care, 2000-2009).

BRIEF DESCRIPTION OF THE FIGURES

FIG. 2a shows the effect of empagliflozin, sibutramine and orlistat both alone and in combination with empagliflozin on glucose tolerance as assessed by changes in the total area under the curve (AUC) for plasma glucose.

FIG. 3a shows the effect of empagliflozin, sibutramine and orlistat both alone and in combination with empagliflozin on the plasma levels of various metabolic parameters on Day 30.

FIG. 3b shows the effect of empagliflozin, sibutramine and orlistat both alone and in combination with empagliflozin on the body composition of DIO rats at the study conclusion.

DETAILED DESCRIPTION

Figure 1:
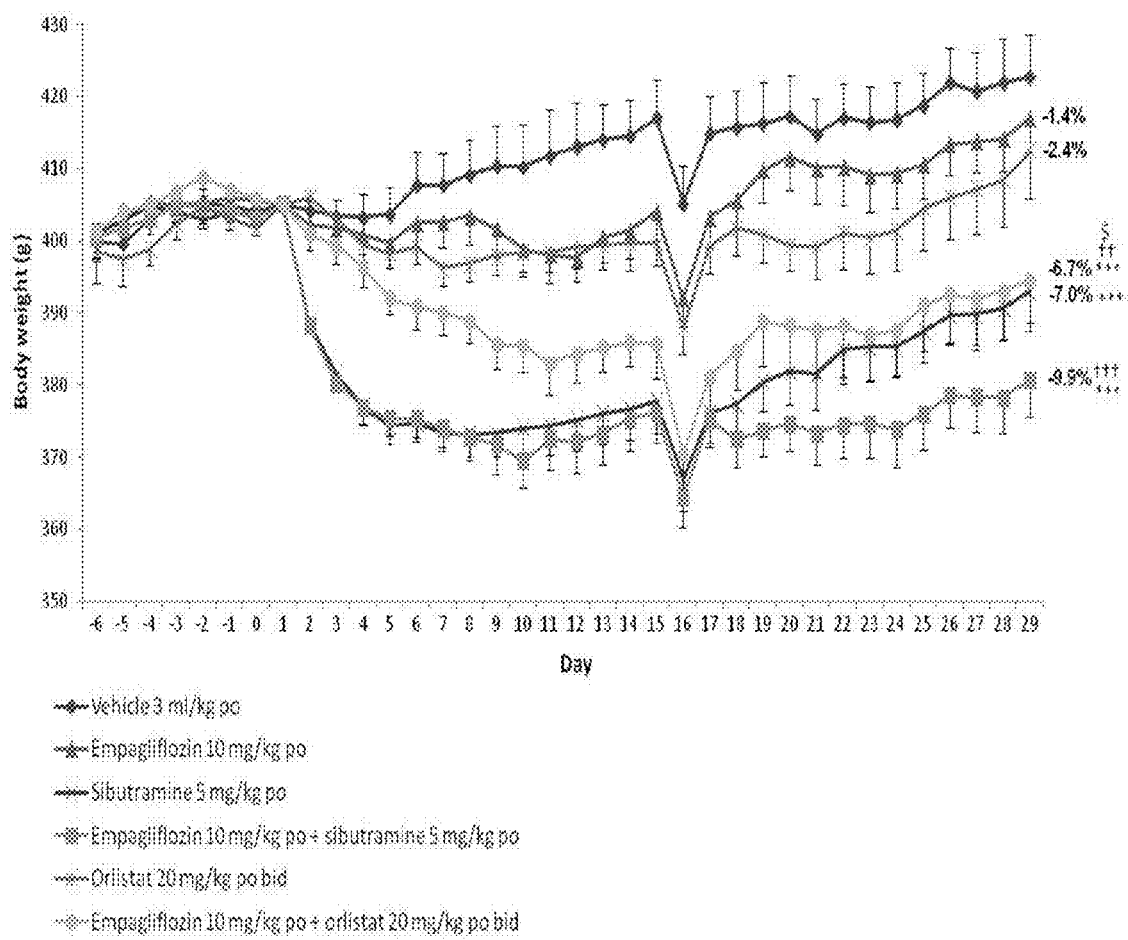
FIG. 1 shows the effect of empagliflozin, sibutramine and orlistat both alone and in combination with empagliflozin on rat body weight.

The aspects according to the present invention, in particular the pharmaceutical compositions, methods and uses, refer to a combination of empagliflozin and one or more antiobesity drugs as defined hereinbefore and hereinafter.

Preferred examples of antiobesity drugs are sibutramine, orlistat, cetilistat, a combination of phentermine and topiramate, a combination of naltrexone and bupropion, lorcaserin, liraglutide. The beforementioned drugs include pharmaceutically acceptable salts thereof or hydrates or solvates thereof.

When this invention refers to patients requiring treatment or prevention, it relates primarily to treatment and prevention in humans, but the pharmaceutical composition may also be used accordingly in veterinary medicine in mammals. In the scope of this invention adult patients are preferably humans of the age of 18 years or older. Also in the scope of this invention, patients are adolescent humans, i.e. humans of age 10 to 17 years, preferably of age 13 to 17 years.

According to an embodiment of this invention the patient is diagnosed of being overweight or obese, including class I, II and/or III obesity, visceral obesity and/or abdominal obesity.

According to an embodiment of this invention the patient is diagnosed of having one or more conditions selected from the group consisting of pre-diabetes, type 2 diabetes mellitus, impaired glucose tolerance (IGT), impaired fasting blood glucose (IFG), hyperglycemia, postprandial hyperglycemia, hyperinsulinemia and metabolic syndrome.

According to an embodiment of this invention the patient is diagnosed of being overweight or obese and is diagnosed of having one or more conditions selected from the group consisting of pre-diabetes, type 2 diabetes mellitus, impaired glucose tolerance (IGT), impaired fasting blood glucose (IFG), hyperglycemia, postprandial hyperglycemia, hyperinsulinemia and metabolic syndrome.

The present invention also discloses the use of the pharmaceutical composition for improving glycemic control in patients being overweight or obese and having type 2 diabetes or showing first signs of pre-diabetes. Thus, the invention also includes diabetes prevention. If therefore a pharmaceutical composition according to this invention is used to improve the glycemic control as soon as one of the above-mentioned signs of pre-diabetes are present in an overweight or obese patient, the onset of manifest type 2 diabetes mellitus can be delayed or prevented in this patient.

The method and/or use according to this invention is advantageously applicable in those patients who show one, two or more of the following conditions:
(a) insufficient glycemic control with diet and exercise alone;
(b) insufficient weight control despite therapy with an antiobesity drug;
(c) insufficient weight control despite therapy with empagliflozin;
(d) insufficient glycemic control despite oral monotherapy with metformin, in particular despite oral monotherapy at a maximal recommended or tolerated dose of metformin.

Furthermore, the method or use according to this invention is advantageously applicable in those patients who show one, two or more of the following conditions:
(a) a fasting blood glucose or serum glucose concentration greater than 100 mg/dL, in particular greater than 125 mg/dL;
(b) a postprandial plasma glucose equal to or greater than 140 mg/dL;
(c) an HbA1c value equal to or greater than 6.5%, in particular equal to or greater than 7.0%, especially equal to or greater than 7.5%, even more particularly equal to or greater than 8.0%.

Furthermore, the method and use according to this invention is particularly suitable in the treatment of patients who are diagnosed of being overweight or obese and having one or more of the following conditions
(a) triglyceride blood level ≥150 mg/dL,
(b) HDL-cholesterol blood level <40 mg/dL in female patients and <50 mg/dL in male patients,
(c) a systolic blood pressure ≥130 mm Hg and a diastolic blood pressure ≥85 mm Hg,
(d) a fasting blood glucose level ≥100 mg/dL.

It is assumed that overweight or obese patients diagnosed with impaired glucose tolerance (IGT), impaired fasting blood glucose (IFG), with insulin resistance and/or with metabolic syndrome suffer from an increased risk of developing a cardiovascular disease, such as for example myocardial infarction, coronary heart disease, heart insufficiency, thromboembolic events. A glycemic control according to this invention may result in a reduction of the cardiovascular risks.

A treatment or use according to this invention is particularly suitable as long term treatment or use as described hereinbefore and hereinafter, in particular in the long term glycemic control in overweight or obese patients, in particular in patients additionally diagnosed of pre-diabetes or type 2 diabetes mellitus. The term "long term" as used hereinbefore and hereinafter indicates a treatment of or administration in a patient within a period of time longer than 12 weeks, preferably longer than 25 weeks, even more preferably longer than 1 year.

Therefore, a particularly preferred embodiment of the present invention provides a method for therapy, preferably oral therapy, for improvement, especially long term improvement, of glycemic control in patients with pre-diabetes or type 2 diabetes mellitus in particular in patients additionally diagnosed of overweight, obesity (including class I, class II and/or class III obesity), visceral obesity and/or abdominal obesity.

Unless otherwise noted, the combination therapy according to the invention may refer to first line, second line or third line therapy, or initial or add-on combination therapy or replacement therapy.

According to one embodiment empagliflozin and the one or more antiobesity drugs are administered in combination, i.e. simultaneously, for example in one single formulation or dosage form or in two separate formulations or dosage forms, or in alternation or sequentially, for example successively in two separate formulations or dosage forms. Hence, the administration of one combination partner, i.e. emagliflozin or the one or more antiobesity drugs, may be prior to, concurrent to, or subsequent to the administration of the other combination partner. In one embodiment, for the combination therapy according to this invention empagliflozin and the one or more antiobesity drugs are administered in different formulations or different dosage forms. In another embodiment, for the combination therapy according to this invention empagliflozin and the one or more antiobesity drugs are administered in the same formulation or in the same dosage form.

In the methods and uses according to the present invention empagliflozin and the one or more antiobesity drugs are administered in combination or alternation or sequentially. The term "administration in combination" means that the active ingredients are administered at the same time, i.e. simultaneously, or essentially at the same time. The term "administration in alternation" means that at first one of the two active ingredients, i.e. empagliflozin or the one or more antiobesity drugs, is administered and after a period of time the other active ingredient, i.e. the one or more antiobesity drugs or empagliflozin, is administered whereby this administration scheme may be repeated one or more times. The period of time between the administration of the first and of the second active ingredient may be in the range from 1 min to 12 hours. The administration which is in combination or in alternation may be once, twice, three times or four times daily, preferably once or twice daily. The term "sequentially" means that to a patient the first active ingredient is administered to the patient one or more times in a first period of time followed by an administration of the second active ingredient which is adminstered to the patient one or more times in a second period of time.

According to the present invention there is provided a pharmaceutical composition comprising empagliflozin and one or more antiobesity drugs and one or more pharmaceutically acceptable excipients.

According to an embodiment of the present invention there is provided a pharmaceutical dosage form comprising empagliflozin and one or more antiobesity drugs and one or more pharmaceutically acceptable excipients.

According to an embodiment the pharmaceutical composition or the pharmaceutical dosage form is provided for oral administration.

A pharmaceutical composition which is present as a separate or multiple dosage form, for example as a kit of parts, is useful in combination therapy to flexibly suit the individual therapeutic needs of the patient. For example a pharmaceutical composition may be present as a first pharmaceutical dosage form comprising empagliflozin and one or more pharmaceutically excipients and a second pharmaceutical dosage form comprising one or more antiobesity drugs and one or more pharmaceutically excipients According to an embodiment of the invention a kit of parts comprises
(a) a first containment containing a dosage form comprising empagliflozin and one or more pharmaceutically acceptable excipients, and
(b) a second containment containing a dosage form comprising the one or more antiobesity drugs and one or more pharmaceutically acceptable excipients.

Within the scope of the present invention, empagliflozin is preferably administered orally or by injection, preferably orally. The one or more antiobesity drugs are preferably administered orally or by injection, preferably orally. Other forms of administration are possible and described for the respective antiobesity drug in the literature.

The effects mentioned above are observed both, when empagliflozin and the one or more antiobesity drugs are administered in combination, for example simultaneously in one single or two separate pharmaceutical dosage forms, and when they are administered in alternation, for example successively in two or three separate pharmaceutical dosage forms.

It will be appreciated that the amount of the pharmaceutical composition according to this invention to be administered to the patient and required for use in treatment or prophylaxis according to the present invention will vary with the route of administration, the nature and severity of the condition for which treatment or prophylaxis is required, the age, weight and condition of the patient, concomitant medication and will be ultimately at the discretion of the attendant physician. In general, however, empagliflozin according to this invention is included in the pharmaceutical composition or dosage form in an amount sufficient that by its administration in combination with the one or more antiobesity drugs the glycemic control in the patient to be treated is improved. Furthermore in general, the one or more antiobesity drugs according to this invention are included in the pharmaceutical composition or dosage form in an amount sufficient that by their administration in combination with empagliflozin the weight control in the patient to be treated is improved.

In the following, preferred ranges of the amount of empagliflozin to be employed in the pharmaceutical compositions, pharmaceutical dosages and treatments according to this invention are described. These ranges refer to the amounts to be administered per day with respect to an adult patient, in particular to a human being, for example of approximately 70 kg body weight, and can be adapted accordingly with regard to an administration 2 times daily and with regard to other routes of administration and with regard to the age of the patient. The ranges of the dosage and amounts are calculated for the active ingredient.

A preferred amount of empagliflozin is in a range from 1 to 50 mg, even more preferably from 1 to 25 mg, even more preferably 5 to 25 mg. Preferred dosages of empagliflozin are for example 1 mg, 2 mg, 2.5 mg, 5 mg, 7.5 mg, 10 mg, 12.5 mg, 15 mg, 20 mg, 25 mg and 50 mg.

A preferred amount of sibutramine is in a range from 5 to 60 mg once daily, even more preferably from 5 to 15 mg. A preferred dosage of sibutramine is for example 10 mg once daily.

A preferred amount of orlistat is in a range from 60 to 400 mg one to three times daily, even more preferably from 60 to 120 mg one to three times daily. A preferred dosage of orlistat is for example 120 mg three times daily, Preferred amounts of further antiobesity drugs are in the range from 1/3 to 1/1 of the respective mono-therapy in the respective administration route.

The amount of empagliflozin and the one or more antiobesity drugs in the pharmaceutical compositions and pharmaceutical dosage forms according to this invention correspond to the respective dosage ranges as provided hereinbefore.

The desired dose of the pharmaceutical composition according to this invention may conveniently be presented in a once daily or as divided dose administered at appropriate intervals, for example as two, three or more doses per day.

The pharmaceutical composition may be formulated for oral, parenteral (including sub-cutaneous) or other routes of administration in liquid or solid form. Oral administration of empagliflozin is preferred. The formulations may, where appropriate, be conveniently presented in discrete dosage units and may be prepared by any of the methods well known in the art of pharmacy. All methods include the step of bringing into association the active ingredient with one or more pharmaceutically acceptable excipients, such as carriers, like liquid carriers or finely divided solid carriers or both, or diluents, and then, if necessary, shaping the product into the desired formulation. Examples of pharmaceutical compositions and pharmaceutical dosage forms comprising empagliflozin and one or more pharmaceutically acceptable excipients are described in WO 2010/092126.

The pharmaceutical composition and the pharmaceutical dosage form preferably comprises one or more pharmaceutical acceptable excipients. Preferred excipients must be "acceptable" in the sense of being compatible with the other ingredients of the formulation and not deleterious to the recipient thereof. Examples of pharmaceutically acceptable excipients are known to the one skilled in the art.

The pharmaceutical composition may be formulated in the form of solutions, suspensions, emulsions, tablets, granules, fine granules, powders, capsules, caplets, soft capsules, pills, oral solutions, syrups, dry syrups, chewable tablets, troches, effervescent tablets, drops, fast dissolving tablets, oral fast-dispersing tablets, etc. According to a preferred embodiment of the present invention there is provided a solid pharmaceutical composition for oral administration. Preferred pharmaceutical dosage form are tablets or capsules.

For further details on dosage forms, formulations and administration of empagliflozin and/or the one or more antiobesity drugs of this invention, reference is made to scientific literature and/or published patent documents, particularly to those cited herein.

The pharmaceutical composition or dosage form may be packaged in a variety of ways. Generally, a manufacture or an article for distribution includes one or more containers that contain the one or more pharmaceutical dosage forms in an appropriate form. Tablets are typically packed in an appropriate primary package for easy handling, distribution and storage and for assurance of proper stability of the composition at prolonged contact with the environment during storage. Primary containers for tablets may be bottles or blister packs.

The manufacture or article may further comprise a label or package insert, which refers to instructions customarily included in commercial packages of therapeutic products, that may contain information about the indications, usage, dosage, administration, contraindications and/or warnings concerning the use of such therapeutic products. In one embodiment, the label or package inserts indicates that the composition can be used for any of the purposes described hereinbefore or hereinafter.

An aspect of the present invention is a manufacture comprising the pharmaceutical composition being present as a pharmaceutical dosage form comprising empagliflozin and the one or more antiobesity drugs and one or more pharmaceutically acceptable excipients.

A further aspect of the present invention is a manufacture comprising the pharmaceutical composition being present as a first and a second pharmaceutical dosage form according to the present invention and a label or package insert comprising instructions that the first and the second pharmaceutical dosage forms are to be administered in combination or alternation or sequentially. Herein the first pharmaceutical dosage form comprises empagliflozin and one or more pharmaceutically excipients and the second pharmaceutical dosage form comprises one or more antiobesity drugs and one or more pharmaceutically excipients.

According to a first embodiment a manufacture comprises (a) a pharmaceutical composition, in particular a solid pharmaceutical dosage form for oral administration, comprising empagliflozin according to the present invention and one or more pharmaceutically acceptable excipients and (b) a label or package insert which comprises instructions that the pharmaceutical composition may or is to be administered, for example in combination or alternation or sequentially, with a medicament comprising one or more antiobesity drugs according to the present invention.

According to a second embodiment a manufacture comprises (a) a pharmaceutical composition comprising one or more antiobesity drugs according to the present invention and one or more pharmaceutically acceptable excipients and (b) a label or package insert which comprises instructions that the pharmaceutical composition may or is to be administered, for example in combination or alternation or sequentially, with a medicament comprising empagliflozin according to the present invention according to the present invention.

The pharmaceutical compositions, dosage forms, methods and uses according to this invention show advantageous effects in the treatment and prevention of those diseases and conditions as described hereinbefore compared with pharmaceutical compositions, dosage forms, methods and uses which comprise only one of the two active ingredients. Additional advantageous effects may be seen for example with respect to efficacy, dosage strength, dosage frequency, pharmacodynamic properties, pharmacokinetic properties, fewer adverse effects, convenience, compliance, etc.

Any of the above mentioned combinations, methods and uses within the scope of the invention may be tested by animal models known in the art. In the following, in vivo experiments are described which are suitable to evaluate pharmacologically relevant properties of pharmaceutical compositions and methods according to this invention: Pharmaceutical compositions and methods according to this invention can be tested in genetically hyperinsulinemic or diabetic animals like db/db mice, ob/ob mice, Zucker Fatty (fa/fa) rats or Zucker Diabetic Fatty (ZDF) rats. In addition, they can be tested in animals with experimentally induced diabetes like HanWistar or Sprague Dawley rats pretreated with streptozotocin.

The effect on glycemic control of the combinations according to this invention can be tested after single dosing empagliflozin and the one or more antiobesity drugs alone and in combination in an oral glucose tolerance test in the animal models described hereinbefore. The time course of blood glucose is followed after an oral glucose challenge in overnight fasted animals. The combinations according to the present invention improve glucose excursion compared to each monotherapy as measured by reduction of peak glucose concentrations or reduction of glucose AUC. In addition, after multiple dosing of empagliflozin and the one or more antiobesity drugs agonist alone and in combination in the animal models described hereinbefore, the effect on glycemic control can be determined by measuring the HbA1c value in blood. The combinations according to this invention may reduce HbA1c compared to each monotherapy.

A superior effect of the combination of empagliflozin and the one or more antiobesity drugs according to the present invention on beta-cell regeneration and neogenesis can be determined after multiple dosing in the animal models described hereinbefore by measuring the increase in pancreatic insulin content, or by measuring increased beta-cell mass by morphometric analysis after immunohistochemical staining of pancreatic sections, or by measuring increased glucose-stimulated insulin secretion in isolated pancreatic islets.

PHARMACOLOGICAL EXAMPLES

The following examples show the beneficial effect on glycemic control, body weight, body composition and further clinical aspects of the combinations and pharmaceutical compositions according to the present invention.

Example 1

Animal In Vivo Experiments Animals

Female Wistar rats (weight range 250-300 g upon arrival) are obtained from Charles River (Margate, Kent) and housed in pairs or threes at a temperature of 21±4° C. and 55±20% humidity. Animals are maintained on a reverse phase light-dark cycle (lights off for 8 h from 09.30-17.30 h) during which time the room is illuminated by red light. Animals have free access to powdered high fat diet (VRF1 plus 20% lard; Special Diet Services (SDS), Witham, UK), ground chocolate (Cadbury's Dairy Milk®), ground peanuts (Big D®, Trigon Snacks Ltd.) and tap water at all times unless specified otherwise. Animals are housed for 20-24 weeks for the induction of obesity. The work reported in this manuscript is performed in accordance with UK law as detailed in the Animals (Scientific Procedures) Act 1986.

Approximately two weeks before the start of the studies, animals are housed singly in polypropylene cages with wire grid floors (so food spillage could be determined). Each cage contains an appropriate amount of paper bedding for warmth, environmental enrichment and to provide an area for animals to get off the wire grid floor.

Animals undergo a baseline period of dosing where each animal is dosed once daily orally with vehicle. Towards the end of this baseline phase, animals are allocated by a Statistician into treatment groups, balanced in regard to baseline body weight and daily food and water intake. Drug dosing is timed to begin at the onset of the dark phase of the light/dark cycle. Rats, feeding jars and water bottles are weighed (to the nearest 0.1 g) every day at the time of administration of vehicle or drug.

Methods

In an initial study, animals are dosed once daily for approximately 4 weeks with vehicle, empagliflozin or with the positive control, sibutramine. Blood samples (4 hour fasted) are taken from the lateral tail vein during the baseline phase and on Days 14 and 28 four hours after dosing and plasma is assayed for various relevant metabolic parameters. On Day 21 animals are dosed and immediately placed in metabolism cages for a 7 hour period. Food is not present in the metabolism cages, although animals have free access to water. Urine is collected and assayed for glucose content using hand-held glucose meters (Abbott Xceed). At the end of the study (Day 29), carcasses are saved for body composition analysis.

In combination studies, sibutramine is dosed once daily with empagliflozin. Orlistat is dosed twice daily: once at the start of the dark phase (in combination with empagliflozin) and again four hours later. Blood samples are taken after approximately 2 and 4 weeks of dosing after a 4 h fast, with the exception of the combination studies with sibutramine and orlistat where samples are taken after an overnight fast. In the studies where empagliflozin is given with either orlistat or sibutramine, animals undergo an oral glucose (2 g/kg) tolerance test on Day 30 after an overnight fast. Blood samples are taken immediately before and 10, 20, 30, 60 and 120 minutes post glucose administration. At the conclusion of each experiment, carcasses are saved for body composition analysis.

Plasma Analysis

Blood is collected in EDTA-coated collection tubes (Sarstedt) and immediately spun in a cooled centrifuge and the plasma stored frozen. Subsequently, plasma is assayed for content of one or more of the following: glucose, insulin, leptin, glycerol, and triacylglycerol (TAG) content. Blood (collected in an EDTA tube and frozen immediately) is assayed for HbA1c.

Commercially available enzyme-linked immunosorbent assays (ELISAs) and colorimetric kits are used to assay glucose (Thermo Electron Corp., PA, USA), insulin (Mercodia, Uppsala, Sweden), glycerol and true triglycerides (Sigma, Mo., USA), and leptin (Assay Designs, MI, USA). HbA1c is assayed by a direct enzymatic assay (Diazyme, CA, USA).

Body Composition Assessment

Carcass composition (body fat, protein and water) is determined using the FoodScan NIR (near infra-red) meat analyser (Foss, UK). Carcasses are milled at the temperature of liquid nitrogen and stored at −20° C. in sealed containers. This method has been demonstrated to produce highly comparable results (correlation coefficient: $r^2=0.95$) to those obtained with the gold standard chemical analysis method of carcass composition.

Statistical Analysis

Statistical analysis is performed by a Statistician. Body weight and food and water intake data are assessed by analysis of covariance (ANCOVA) with treatment as a factor, and baseline data as the covariate. In the case of body weight analysis, Day 1 body weight (i.e. the weight immediately before the first drug treatment) is the covariate. In the case of the food and water intake analysis, the covariate is the average daily intake during the baseline phase of the study.

Plasma data are analysed by a general linear model with treatment as a factor. Where appropriate, data undergo a log transformation prior to analysis. Baseline plasma data and Day 1 body weight are included as covariates. HbA1c data are analysed by a robust regression model using M estimation (Huber weighting, using the default parameter c=1.345). Baseline HbA1c levels and Day 1 body weight are included as covariates. Since no differences are observed between the two and four week changes in plasma parameters, only the final plasma data for each study is detailed.

Carcass composition data are analysed by robust regression with treatment as factors. Day 1 body weight is included as a covariate.

Means detailed in the figures and tables are adjusted for differences at baseline (see above). SEM are calculated from the residuals of the statistical model. Comparisons between groups are by William's test or the multiple t test as deemed appropriate. A value of $p<0.05$ is regarded as being statistically significant. All statistical analysis is performed using SAS version 9.1.3 (SAS Institute Inc., Cary, N.C., USA).

Results

The effect of sibutramine to reduce body weight in DIO rats ($p<0.001$) is increased by co-treatment with empagliflozin (weight loss increased from 7.0% compared with vehicle-treated controls to 9.9%; FIG. 1). Empagliflozin significantly augments (from 2.4% compared with vehicle-treated controls on Day 29 to 6.7%) the effect of orlistat on body weight ($p<0.05$; FIG. 1). Both sibutramine ($p<0.05$) and orlistat ($p<0.05$) reduce plasma leptin and, in both cases, this reduction is further increased in the presence of empagliflozin ($p<0.001$; FIG. 3a).

Figure 2B:
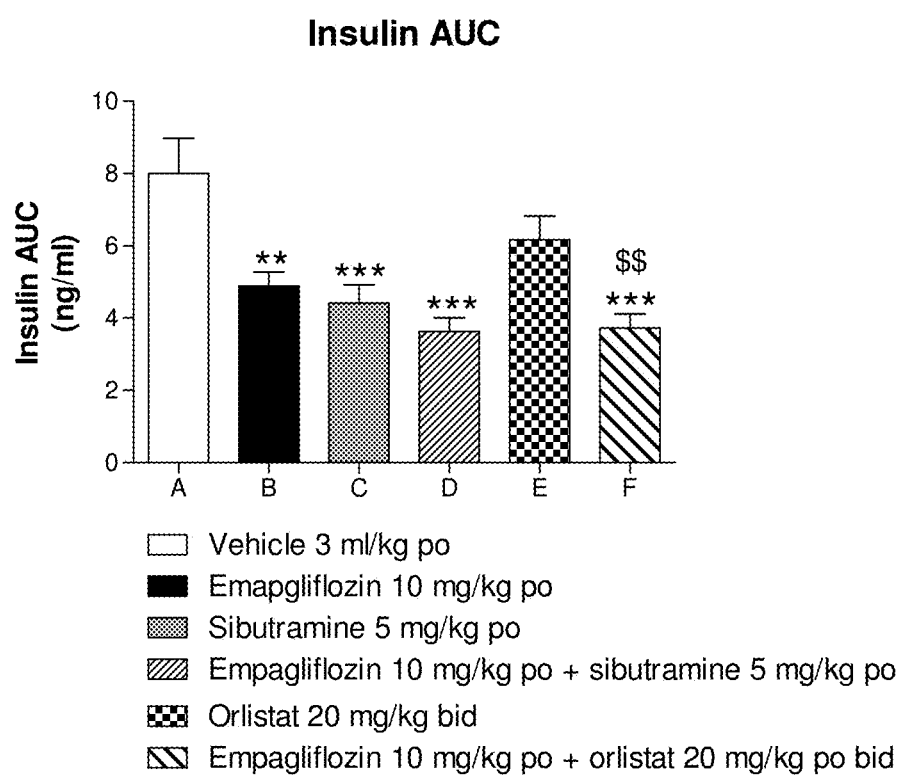
FIG. 2b shows the effect of empagliflozin, sibutramine and orlistat both alone and in combination with empagliflozin on glucose tolerance as assessed by changes in the plasma insulin.

Empagliflozin (p<0.01) and sibutramine (p<0.001) significantly improve glucose tolerance (glucose AUC) when administered either alone or in combination (p<0.001; FIG. 2a) for 30 days. The effect of the combination treatment is not significantly different to that of individual drug treatments (FIG. 2a). Orlistat does not significantly affect glucose tolerance, although a significant reduction in the glucose AUC is observed when orlistat is administered in combination with empagliflozin (p<0.05; FIG. 2a). During OGTT, AUC of Insulin with empagliflozin and orlistat are reduced significantly while it is not significantly decreased with orlistat alone. When orlistat is combined with empagliflozin the AUC insulin becomes significantly reduced in comparison to vehicle or to orlistat alone. These diminution in insulin level reflects an improvement in insulin sensitivity.

After 30 days of treatment, both empagliflozin and sibutramine significantly reduce plasma insulin (p<0.05 and p<0.001, respectively; FIG. 3a) when administered alone though only sibutramine significantly reduces plasma glucose (p<0.001). The combination of empagliflozin with sibutramine significantly reduce plasma glucose (p<0.001), insulin (p<0.001), TAG (p<0.05) and leptin (p<0.001) compared to vehicle-treated controls at Day 30 (FIG. 3a). At Day 30, the combination of empagliflozin and orlistat significantly reduces plasma glucose (p<0.01), insulin (p<0.001).

Empagliflozin does not significantly affect body composition; however, sibutramine and orlistat both significantly and selectively reduce carcass fat (p<0.01; FIG. 3b). When dosed in combination, the reduction in body fat (p<0.001) induced by empagliflozin and sibutramine is greater than that observed with either drug alone (FIG. 3b). The combination of orlistat and empagliflozin significantly reduces body fat (p<0.01) although the effect is not significantly different to that observed with orlistat alone (FIG. 3b).

Discussion

Consistent with the reported effect of the drug in diabetic animals, empagliflozin significantly reduces plasma glucose in the present study. However, these effects are small and not dose-dependent in this particular model. Since the cafeteria fed rats exhibit plasma glucose and blood HbA1c levels within a normal range, it is not unexpected that the drug would have marginal effects in the present studies. Although the cafeteria-fed animals are not diabetic, they exhibit insulin resistance characterised by a moderate hyperinsulinaemia. Chronic empagliflozin treatment tends to have either a small effect to reduce plasma insulin or no impact. In contrast, sibutramine reduces plasma insulin indicative of the animals exhibiting improved insulin sensitivity upon chronic drug treatment. Furthermore empagliflozin and also the SNRI, sibutramine, both improve glucose tolerance (without stimulating insulin secretion) as illustrated by significant reductions in the glucose and insulin AUC in an oral glucose tolerance test. The improvements in glucose tolerance and plasma insulin in the case of the antiobesity agent, sibutramine, are likely to be secondary to the weight loss induced by the compound.

Combination of empagliflozin with sibutramine or orlistat augments the effects of the drugs to reduce body weight. The reason for these effects is likely to be due to the loss of calories through the urine and/or direct effects on food intake caused by empagliflozin. Combining empagliflozin with sibutramine or orlistat may have the advantage of dosing a therapy designed to directly control hyperglycaemia in addition to increasing the action of the other therapy to reduce body weight with the commensurate benefits on insulin sensitivity and glucose control subsequently manifest.

Example 2

Treatment of Pre-Diabetes

The efficacy of a combination treatment comprising empagliflozin and one or more antiobesity drugs in the treatment of pre-diabetes characterised by pathological fasting glucose and/or impaired glucose tolerance can be tested using clinical studies. In studies over a shorter period (e.g. 2-4 weeks) the success of the treatment is examined by determining the fasting glucose values and/or the glucose values after a meal or after a loading test (oral glucose tolerance test or food tolerance test after a defined meal) after the end of the period of therapy for the study and comparing them with the values before the start of the study and/or with those of a placebo group. In addition, the fructosamine value can be determined before and after therapy and compared with the initial value and/or the placebo value. A significant drop in the fasting or non-fasting glucose levels demonstrates the efficacy of the treatment. In studies over a longer period (12 weeks or more) the success of the treatment is tested by determining the HbA1c value, by comparison with the initial value and/or with the value of the placebo group. A significant change in the HbA1c value compared with the initial value and/or the placebo value demonstrates the efficacy of the pharmaceutical composition according to the invention for treating pre-diabetes.

Example 3

Preventing Manifest Type 2 Diabetes Mellitus
Mellitus

Treating patients with pathological fasting glucose and/or impaired glucose tolerance (pre-diabetes) is also in pursuit of the goal of preventing the transition to manifest type 2 diabetes mellitus. The efficacy of a treatment according to the present invention can be investigated in a comparative clinical study in which pre-diabetes patients are treated over a lengthy period (e.g. 1-5 years) with either a combination according to this invention or with placebo or with a non-drug therapy or other medicaments. During and at the end of the therapy, by determining the fasting glucose and/or a loading test (e.g. oGTT), a check is made to determine how many patients exhibit manifest type 2 diabetes, i.e. a fasting glucose level of >125 mg/dl and/or a 2 h value according to oGTT of >199 mg/dl. A significant reduction in the number of patients who exhibit manifest type 2 diabetes when treated with a combination according to this invention as compared to one of the other forms of treatment, demonstrates the efficacy in preventing a transition from pre-diabetes to manifest type 2 diabetes mellitus.

Example 4

Treatment of Type 2 Diabetes Mellitus

Treating patients with type 2 diabetes mellitus with a combination according to the invention, in addition to producing an acute improvement in the glucose metabolic situation, prevents a deterioration in the metabolic situation in the long term. This can be observed is patients are treated for a longer period, e.g. 3 months to 1 year or even 1 to 6 years, with a combination according to the invention and are compared with patients who have been treated with other antidiabetic and/or antiobesity medicaments. There is evidence of therapeutic success compared with other treatments if no or only a slight increase in the fasting glucose and/or HbA1c value is observed. Further evidence of therapeutic success is obtained if a significantly smaller percentage of the patients treated with a combination according to the invention, compared with patients who have received another treatment, undergo a deterioration in the glucose metabolic position (e.g. an increase in the HbA1c value to >6.5% or >7%) to the point where treatment with an (additional) oral antidiabetic medicament or with insulin or with an insulin analogue is indicated.

Example 5

Treatment of Insulin Resistance

In clinical studies running for different lengths of time (e.g. 2 weeks to 12 months) the success of the treatment is checked using a hyperinsulinaemic euglycaemic glucose clamp study. A significant rise in the glucose infusion rate at the end of the study, compared with the initial value or compared with a placebo group, or a group given a different therapy, proves the efficacy of a treatment according to the invention in the treatment of insulin resistance.

Example 6

Treatment of Hyperglycaemia

In clinical studies running for different lengths of time (e.g. 1 day to 24 months) the success of the treatment in patients with hyperglycaemia is checked by determining the fasting glucose or non-fasting glucose (e.g. after a meal or a loading test with oGTT or a defined meal). A significant fall in these glucose values during or at the end of the study, compared with the initial value or compared with a placebo group, or a group given a different therapy, proves the efficacy of a combination treatment according to the invention in the treatment of hyperglycaemia.

Example 7

Prevention of Micro- or Macrovascular Complications

The treatment of type 2 diabetes or pre-diabetes patients with a combination according to the invention prevents or reduces or reduces the risk of developing microvascular complications (e.g. diabetic neuropathy, diabetic retinopathy, diabetic nephropathy, diabetic foot, diabetic ulcer) or macrovascular complications (e.g. myocardial infarct, acute coronary syndrome, unstable angina pectoris, stable angina pectoris, stroke, peripheral arterial occlusive disease, cardiomyopathy, heart failure, heart rhythm disorders, vascular restenosis). Type 2 diabetes or patients with pre-diabetes are treated long-term, e.g. for 1-6 years, with a combination treatment according to the invention and compared with patients who have received another treatment or with placebo. Evidence of the therapeutic success compared with patients who have received another treatment or with placebo can be found in the smaller number of single or multiple complications. In the case of macrovascular events, diabetic foot and/or diabetic ulcer, the numbers are counted by anamnesis and various test methods. In the case of diabetic retinopathy the success of the treatment is determined by computer-controlled illumination and evaluation of the background to the eye or other ophthalmic methods. In the case of diabetic neuropathy, in addition to anamnesis and clinical examination, the nerve conduction rate can be measured using a calibrated tuning fork, for example. With regard to diabetic nephropathy the following parameters may be investigated before the start, during and at the end of the study: secretion of albumin, creatinin clearance, serum creatinin values, time taken for the serum creatinin values to double, time taken until dialysis becomes necessary.

Example 8

Treatment of Metabolic Syndrome

The efficacy of a combination treatment according to the invention can be tested in clinical studies with varying run times (e.g. 12 weeks to 6 years) by determining the fasting glucose or non-fasting glucose (e.g. after a meal or a loading test with oGTT or a defined meal) or the HbA1c value. A significant fall in these glucose values or HbA1c values during or at the end of the study, compared with the initial value or compared with a placebo group, or a group given a different therapy, proves the efficacy of an active substance in the treatment of Metabolic Syndrome. Examples of this are a reduction in systolic and/or diastolic blood pressure, a lowering of the plasma triglycerides, a reduction in total or LDL cholesterol, an increase in HDL cholesterol or a reduction in weight, either compared with the starting value at the beginning of the study or in comparison with a group of patients treated with placebo or a different therapy.

Example of Pharmaceutical Composition and Dosage Form

The following example of solid pharmaceutical compositions and dosage forms for oral administration serves to illustrate the present invention more fully without restricting it to the contents of the example. Further examples of compositions and dosage forms for oral administration, are described in WO 2010/092126. The term "active substance" denotes empagliflozin according to this invention, especially its crystalline form as described in WO 2006/117359 and WO 2011/039107.

Tablets containing 2.5 mg, 5 mg, 10 mg, 25 mg, 50 mg of active substance

|  | Active substance | | | | |
| --- | --- | --- | --- | --- | --- |
|  | 2.5 mg/per tablet | 5 mg/per tablet | 10 mg/per tablet | 25 mg/per tablet | 50 mg/per tablet |
| Wet granulation | | | | | |
| active substance | 2.5000 | 5.000 | 10.00 | 25.00 | 50.00 |
| Lactose Monohydrate | 40.6250 | 81.250 | 162.50 | 113.00 | 226.00 |
| Microcrystalline Cellulose | 12.5000 | 25.000 | 50.00 | 40.00 | 80.00 |
| Hydroxypropyl Cellulose | 1.8750 | 3.750 | 7.50 | 6.00 | 12.00 |
| Croscarmellose Sodium | 1.2500 | 2.500 | 5.00 | 4.00 | 8.00 |
| Purified Water | q.s. | q.s. | q.s. | q.s. | q.s. |
| Dry Adds | | | | | |
| Microcrystalline Cellulose | 3.1250 | 6.250 | 12.50 | 10.00 | 20.00 |
| Colloidal silicon dioxide | 0.3125 | 0.625 | 1.25 | 1.00 | 2.00 |
| Magnesium stearate | 0.3125 | 0.625 | 1.25 | 1.00 | 2.00 |
| Total core | 62.5000 | 125.000 | 250.00 | 200.00 | 400.00 |

-continued

|  | Active substance | | | | |
| --- | --- | --- | --- | --- | --- |
|  | 2.5 mg/per tablet | 5 mg/per tablet | 10 mg/per tablet | 25 mg/per tablet | 50 mg/per tablet |
| Film Coating | | | | | |
| Film coating system | 2.5000 | 4.000 | 7.00 | 6.00 | 9.00 |
| Purified Water | q.s. | q.s. | q.s. | q.s. | q.s. |
| Total | 65.000 | 129.000 | 257.00 | 206.00 | 409.00 |

Details regarding the manufacture of the tablets, the active pharmaceutical ingredient, the excipients and the film coating system are described in WO 2010/092126, in particular in the Examples 5 and 6, which hereby is incorporated herein in its entirety.

The invention claimed is:

1. A method for slowing the progression of, delaying or treating of pre-diabetes in a patient diagnosed of being overweight or obese comprising administering empagliflozin and one or more antiobesity drugs to the patient, wherein the one or more anti-obesity drug is selected from the group consisting of cetilistat, a combination of phentermine and topiramate, and lorcaserin.

2. A method for preventing, slowing the progression of, delaying or treating a metabolic disorder selected from the group consisting of type 2 diabetes mellitus, impaired glucose tolerance, impaired fasting blood glucose, hyperglycemia, postprandial hyperglycemia, hyperinsulinemia and metabolic syndrome in a patient diagnosed of being overweight or obese comprising administering empagliflozin and one or more antiobesity drugs to the patient, wherein the one or more anti-obesity drug is selected from the group consisting of cetilistat, a combination of phentermine and topiramate, and lorcaserin.

3. A method for preventing, slowing the progression of, delaying or treating of an onset of type 2 diabetes mellitus in a patient diagnosed of being overweight or obese comprising administering empagliflozin and one or more antiobesity drugs to the patient, wherein the one or more anti-obesity drug is selected from the group consisting of cetilistat, a combination of phentermine and topiramate, and lorcaserin.

4. A method for treating of overweight or obesity in a patient diagnosed of having one or more conditions selected from the group consisting of pre-diabetes, type 2 diabetes mellitus, impaired glucose tolerance, impaired fasting blood glucose, hyperglycemia, postprandial hyperglycemia, hyperinsulinemia and metabolic syndrome comprising administering empagliflozin and one or more antiobesity drugs to the patient, wherein the one or more anti-obesity drug is selected from the group consisting of cetilistat, a combination of phentermine and topiramate, and lorcaserin.

5. A method for improving glycemic control and/or for reducing of fasting plasma glucose, of postprandial plasma glucose and/or of glycosylated hemoglobin HbA1c in a patient diagnosed of being overweight or obese comprising administering empagliflozin and one or more antiobesity drugs to the patient, wherein the one or more anti-obesity drug is selected from the group consisting of cetilistat, a combination of phentermine and topiramate, and lorcaserin.

6. A method for preventing, slowing, delaying or reversing progression from impaired glucose tolerance, impaired fasting blood glucose, insulin resistance or from metabolic syndrome to type 2 diabetes mellitus in a patient diagnosed of being overweight or obese comprising administering empagliflozin and one or more antiobesity drugs to the patient, wherein the one or more anti-obesity drug is selected from the group consisting of cetilistat, a combination of phentermine and topiramate, and lorcaserin.

7. A method for preventing, slowing the progression of, delaying or treating of a condition or disorder selected from the group consisting of complications of diabetes mellitus and micro- and macrovascular diseases, in a patient diagnosed of being overweight or obese comprising administering empagliflozin and one or more antiobesity drugs to the patient, wherein the one or more anti-obesity drug is selected from the group consisting of cetilistat, a combination of phentermine and topiramate, and lorcaserin.

8. A method for reducing body weight and/or body fat, or preventing an increase in body weight and/or body fat, or facilitating a reduction in body weight and/or body fat, in a patient diagnosed of being overweight or obese comprising administering empagliflozin and one or more antiobesity drugs to the patient, wherein the one or more anti-obesity drug is selected from the group consisting of cetilistat, a combination of phentermine and topiramate, and lorcaserin.

9. A method for preventing, slowing, delaying or treating diseases or conditions attributed to an abnormal accumulation of ectopic fat, in a patient diagnosed of being overweight or obese comprising administering empagliflozin and one or more antiobesity drugs to the patient, wherein the one or more anti-obesity drug is selected from the group consisting of cetilistat, a combination of phentermine and topiramate, and lorcaserin.

10. A pharmaceutical composition comprising empagliflozin and one or more antiobesity drugs and one or more pharmaceutically acceptable excipients, wherein the one or more anti-obesity drug is selected from the group consisting of cetilistat, a combination of phentermine and topiramate, and lorcaserin.

11. A pharmaceutical dosage form comprising a pharmaceutical composition according to the claim 10.

12. The method according to claim 7, wherein said complications of diabetes mellitus are cataracts.

13. The method according to claim 7, wherein said micro- and macrovascular diseases are selected from the group consisting of nephropathy, retinopathy, neuropathy, tissue ischaemia, diabetic foot, dyslipidemia, arteriosclerosis, myocardial infarction, accute coronary syndrome, unstable angina pectoris, stable angina pectoris, stroke, peripheral arterial occlusive disease, cardiomyopathy, heart failure, heart rhythm disorders and vascular restenosis.

14. The method according to claim 9, wherein said ectopic fat is liver fat.

* * * * *